United States Patent
Huwais

(10) Patent No.: US 9,918,764 B2
(45) Date of Patent: Mar. 20, 2018

(54) IMPLANT/ANCHOR FOR CELLULAR AND VISCO-ELASTIC MATERIALS

(71) Applicant: Huwais IP Holding LLC, Jackson, MI (US)

(72) Inventor: Salah Huwais, Jackson, MI (US)

(73) Assignee: Huwais IP Holding LLC, Jackson, MI (US)

( * ) Notice: Subject to any disclaimer, the term of this patent is extended or adjusted under 35 U.S.C. 154(b) by 317 days.

(21) Appl. No.: 14/646,520

(22) PCT Filed: Dec. 11, 2013

(86) PCT No.: PCT/US2013/074384
§ 371 (c)(1),
(2) Date: May 21, 2015

(87) PCT Pub. No.: WO2014/093487
PCT Pub. Date: Jun. 19, 2014

(65) Prior Publication Data
US 2015/0297275 A1    Oct. 22, 2015

Related U.S. Application Data

(60) Provisional application No. 61/735,558, filed on Dec. 11, 2012.

(51) Int. Cl.
*A61B 17/86* (2006.01)
*A61C 8/00* (2006.01)
*A61B 17/70* (2006.01)

(52) U.S. Cl.
CPC ............ *A61B 17/863* (2013.01); *A61C 8/005* (2013.01); *A61C 8/006* (2013.01); *A61C 8/0025* (2013.01);

(Continued)

(58) Field of Classification Search
CPC ...... A61B 17/863; A61C 8/0025; A61C 8/005
See application file for complete search history.

(56) References Cited

U.S. PATENT DOCUMENTS 2,489,179 A    11/1949  Hartman
5,489,179 A    2/1996   Gabriel et al.
(Continued)

FOREIGN PATENT DOCUMENTS

CN    2232727    8/1996
CN    2318985    5/1999
(Continued)

*Primary Examiner* — Christian Sevilla
(74) *Attorney, Agent, or Firm* — Endurance Law Group PLC

(57) ABSTRACT

An anchoring implant to be screwed into a hole and self-lock therein with secure stability. The implant, which may be used in dental, orthopedic or any of several non-medical applications, has a conically tapered profile with an aggressively-threaded, self-tapping apical end. A central region of the implant is formed with a plurality of burnishing edges each configured to apply a circumferentially sweeping compressive strain to the interior surface of the hole with a burnishing action while the implant is being screwed into position. A coronal end of the implant includes a corking feature to avert mushrooming around the perimeter of the hole. A central thread profile may extend through and intersect the burnishing edges to provide either enhanced self-tapping or enhanced corking functionality. The extreme coronal end comprises a platform for receiving an abutment or other fastening element via an internal connect feature.

20 Claims, 16 Drawing Sheets

(52) U.S. Cl.
CPC ....... *A61B 17/7001* (2013.01); *A61B 17/8645* (2013.01)

(56) References Cited

U.S. PATENT DOCUMENTS

| | | | |
|---|---|---|---|
| 5,536,127 A | 7/1996 | Pennig | |
| 5,702,443 A * | 12/1997 | Brånemark | A61B 17/8625 411/387.3 |
| 5,816,812 A | 10/1998 | Kownacki et al. | |
| 5,891,146 A * | 4/1999 | Simon | A61B 17/863 411/414 |
| 6,048,204 A | 4/2000 | Klardie et al. | |
| 6,149,432 A | 11/2000 | Shaw et al. | |
| 6,264,677 B1 * | 7/2001 | Simon | A61B 17/0401 411/414 |
| 6,402,515 B1 | 6/2002 | Palti et al. | |
| 6,641,395 B2 | 11/2003 | Kumar et al. | |
| 6,679,701 B1 | 1/2004 | Blacklock | |
| 7,008,227 B2 | 3/2006 | Carmichael et al. | |
| 7,300,281 B2 | 11/2007 | Cantatore et al. | |
| 9,326,778 B2 | 5/2016 | Huwais | |
| 2003/0165795 A1 | 9/2003 | Stucki-McCormick | |
| 2004/0223830 A1 | 11/2004 | Panasik et al. | |
| 2004/0230195 A1 | 11/2004 | Kaikkonen et al. | |
| 2005/0118550 A1 | 6/2005 | Turri | |
| 2005/0273110 A1 | 12/2005 | Boehm et al. | |
| 2006/0018733 A1 | 1/2006 | Dill et al. | |
| 2006/0111724 A1 | 5/2006 | Ping | |
| 2007/0037117 A1 | 2/2007 | Jaunberzins | |
| 2007/0099153 A1 | 5/2007 | Fromovich | |
| 2009/0136898 A1 | 5/2009 | Kim | |
| 2009/0142731 A1 | 6/2009 | Kim | |
| 2009/0259227 A1 | 10/2009 | Ahn | |
| 2010/0055645 A1 | 3/2010 | Mullaly et al. | |
| 2010/0330534 A1 | 12/2010 | Hyun | |
| 2012/0197311 A1 | 8/2012 | Kirschman | |
| 2012/0244497 A1 | 9/2012 | Huwais | |
| 2015/0297275 A1 | 10/2015 | Huwais | |

FOREIGN PATENT DOCUMENTS

| | | |
|---|---|---|
| CN | 1246040 A | 3/2000 |
| CN | 2724645 | 9/2005 |
| CN | 101229072 A | 7/2008 |
| CN | 101292906 A | 10/2008 |
| EP | 0530160 A1 | 3/1993 |
| EP | 1273273 A2 | 1/2003 |
| EP | 1749498 A1 | 2/2007 |
| EP | 1752109 B1 | 10/2010 |
| KR | 101128730 B1 | 3/2012 |
| WO | 2007086622 A1 | 8/2007 |
| WO | 2011053588 A1 | 5/2011 |
| WO | 2015172842 A1 | 11/2015 |

* cited by examiner

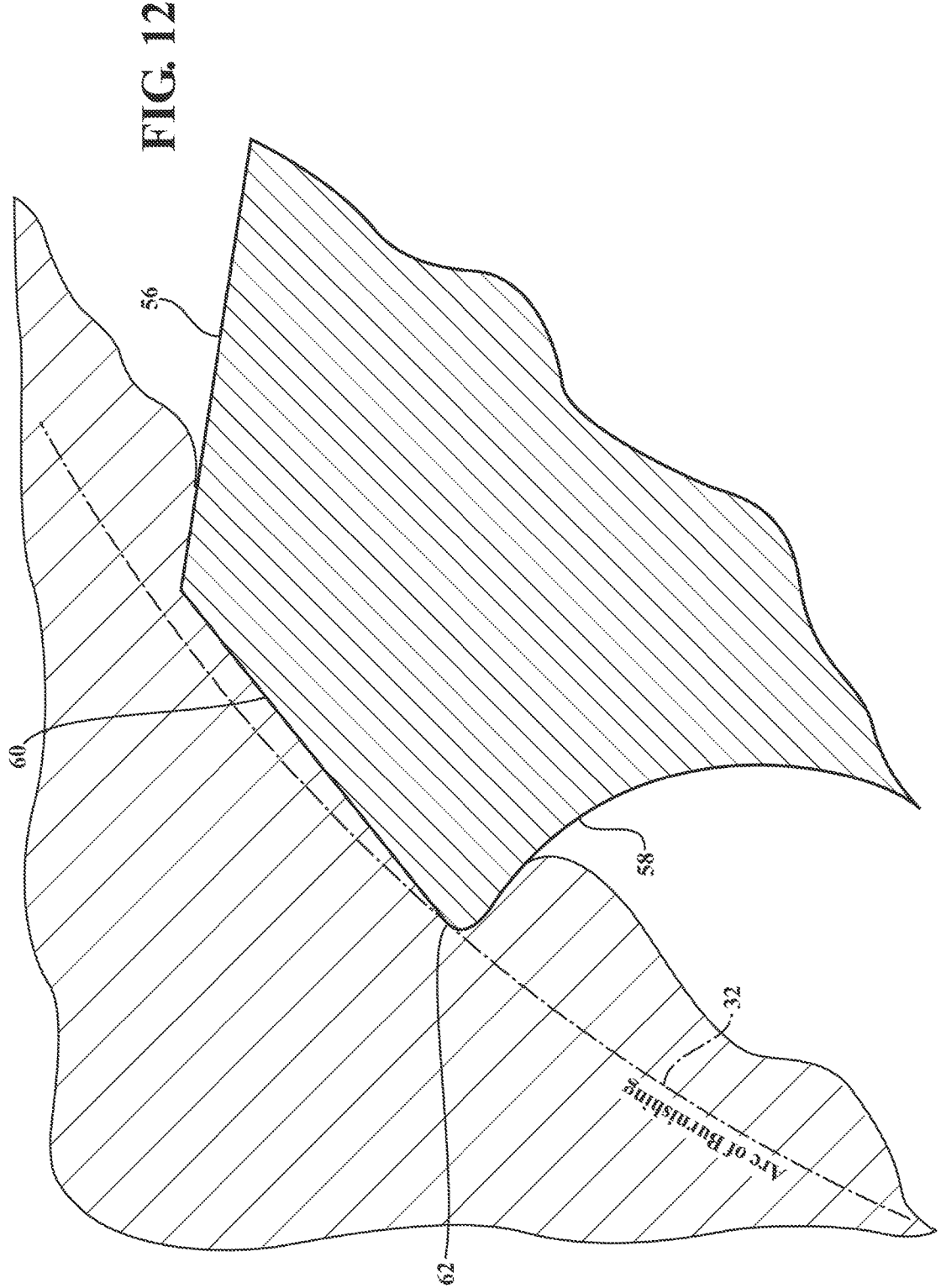

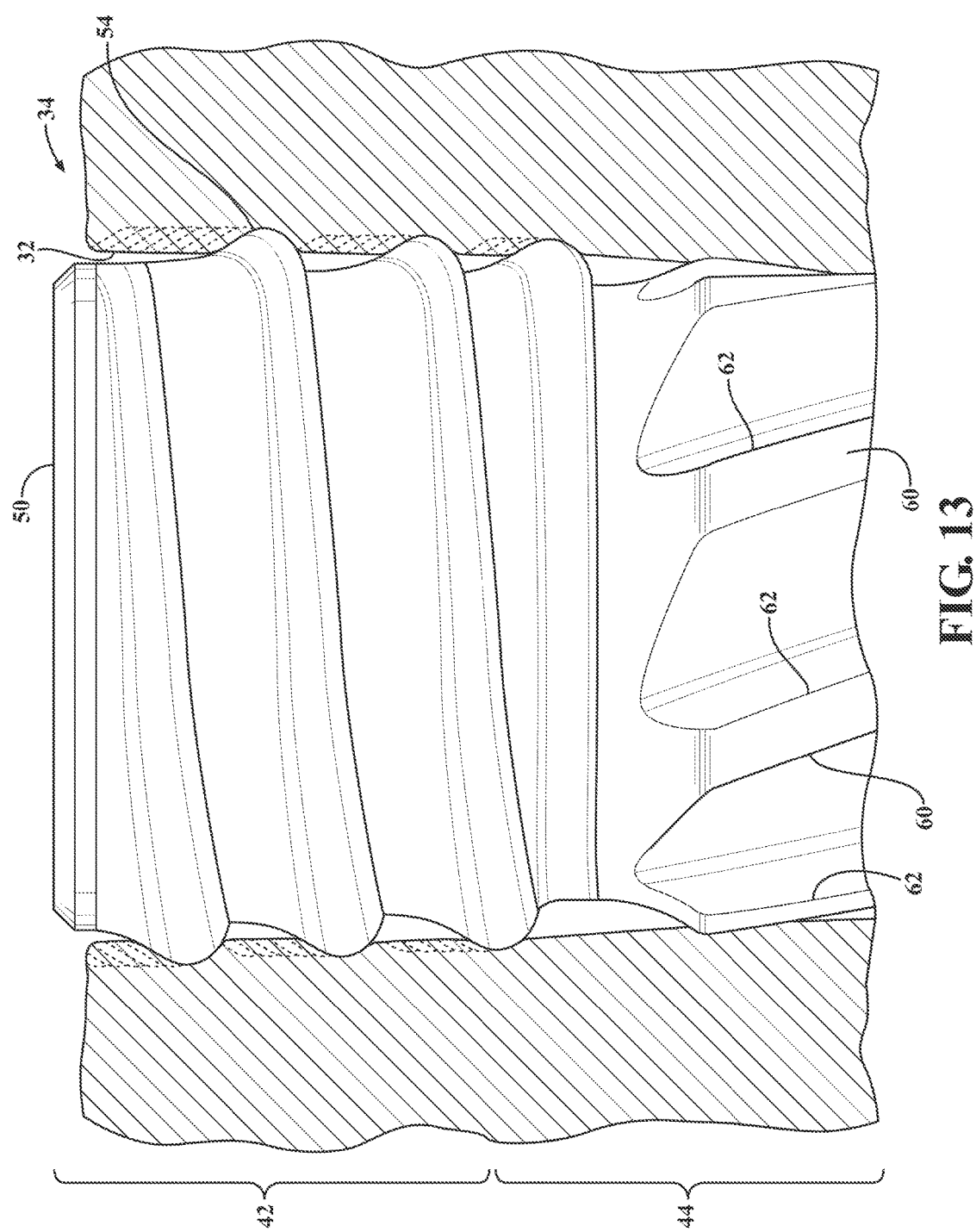

IMPLANT/ANCHOR FOR CELLULAR AND VISCO-ELASTIC MATERIALS

CROSS REFERENCE TO RELATED APPLICATIONS

This application claims priority to Provisional Patent Application No. 61/735,558 filed Dec. 11, 2012, the entire disclosure of which is hereby incorporated by reference and relied upon.

BACKGROUND OF THE INVENTION

1. Field of the Invention

The invention relates generally to implants intended to provide anchorage in a relatively soft or fragile material for a fastener, and more particularly to bone anchorage implants having a combination of features designed to produce bone condensation concurrently with insertion.

2. Description of Related Art

A dental implant (also known as an endosteal implant or fixture) is a surgical device, used to replace one or more missing teeth by fusing to bone and supporting a crown, bridge of teeth, denture, facial prosthetic or to act as an orthodontic anchor. Typically, such implants are designed as threaded, tapered implants that are not loaded immediately after setting in order that full stability may be reached over time as the surrounding bone grows into the crevices of and around the implant. Several months are typically required for bone ingrown until the implant reaches sufficient stability to be put into full service.

Somewhat similar to the dental applications, orthopedic implants are used in other medial situations to replace a missing joint or bone or to support a damaged bone or to provide an anchor point for a fastener. Among the most common types of medical implants are pins, rods, screws and plates used to anchor fractured bones while they heal. Types of internal fixators include bone screws and metal plates, pins, rods, Kirschner wires and intramedullary devices such as the Kuntscher nail and interlocking nail.

In both dental and orthopedic applications, reaching full (or at least sufficient) implant stability to enable loading is a key consideration. The faster an implant can reach sufficient stability, the better. And implants that possess sufficient stability at the time of initial placement are highly valued. The prior art is composed of a great many different designs and concepts aimed at improving implant stability—both initial and long-term. Prior art approaches toward this end have included attention to thread shape, surface texture, coatings to promote osseo-integration, and the like. Implant stability is thus a long-felt need in the art with improvements readily embraced as a testimony to the need for continued improvement.

BRIEF SUMMARY OF THE INVENTION

According to one aspect of this invention, a bone implant is provided of the type that is screwed into an osteotomy. The implant has a body with a conically tapered profile. The body includes an apical end and a coronal end. A central region of the body extends between the apical end and the coronal end. The apical end has an apical thread profile configured to advance the body progressively deeper into the osteotomy as the body is forcibly turned in a first rotary direction. The central region includes at least one longitudinally extending burnishing edge configured to apply a circumferentially sweeping compressive strain to the interior surface of the osteotomy with a burnishing action while the implant is being screwed into position.

According to another aspect of this invention, an implant for any type of application that is screwed into a hole is provided. The implant comprises a body having a conically tapered profile. The body has an apical end and a coronal end. A central region of the body extends between the apical end and the coronal end. The apical end has an apical thread profile defined by a helical twist in a first rotary direction for advancing the body progressively deeper into the hole as the body is forcibly turned in the first rotary direction. The central region includes a plurality of burnishing edges each configured to apply a circumferentially sweeping compressive strain to the interior surface of the hole with a burnishing action while the implant is being screwed into position.

According to yet another aspect of this invention, a method is provided for screwing an implant into an osteotomy. The method comprises the steps of: inserting an apical end of an implant body into the opening of an osteotomy, screwing the body progressively deeper into the osteotomy, and applying a circumferentially sweeping compressive strain to the interior surface of the osteotomy with at least one burnishing edge while concurrently with the screwing step.

As the one or more burnishing edges drag across the inner surface of the hole, stresses applied through the burnishing edges accumulate in the side walls. When the implant reaches full depth in the hole and stops rotating, the built-up stresses begin to fill in around the burnishing edges. This almost immediate elastic response of the bone or other material surrounding the hole provides a favorable high initial implant stability. Continued adaptation of the bone or other material into the crevices of the implant effectively self-locks the implant in position so that it cannot be easily removed by unscrewing. Furthermore, the burnishing edges condense and densify the surrounding walls of the hole, thereby enhancing initial implant stability. A still further advantage provided by the one or more burnishing edges is its ability to strengthen the surrounding material or bone through the introduction of stresses between the material's yield point and its ultimate tensile strength, thereby provoking strain hardening, which occurs because of dislocation movements and dislocation generation within the crystal structure of the material. And yet another benefit of this implant with burnishing edges when used in bone applications is its ability to activate natural bone re-generation. In bone, a permanent change in shape is believed to be associated with micro-cracks that allow energy release, a natural defense mechanism of living bone. This energy release naturally activates bone regeneration for successful long-term implant stability.

In dental and orthopedic applications, an implant according to this invention is capable of reaching sufficient implant stability at the time of initial placement. Furthermore, because of its unique ability to promote bone regeneration, long-term implant stability is both enhanced and accelerated. The unique burnishing attributes of this invention are compatible with many of the prior art variations in thread shape, surface texture and/or special coatings.

BRIEF DESCRIPTION OF THE SEVERAL VIEWS OF THE DRAWINGS

These and other features and advantages of the present invention will become more readily appreciated when considered in connection with the following detailed description and appended drawings, wherein:

FIG. 12 is cross-section taken generally along lines 12-12 of FIG. 11;

FIG. 13 is cross-section taken generally along lines 13-13 of FIG. 11;

DETAILED DESCRIPTION OF THE INVENTION

Figure 3:
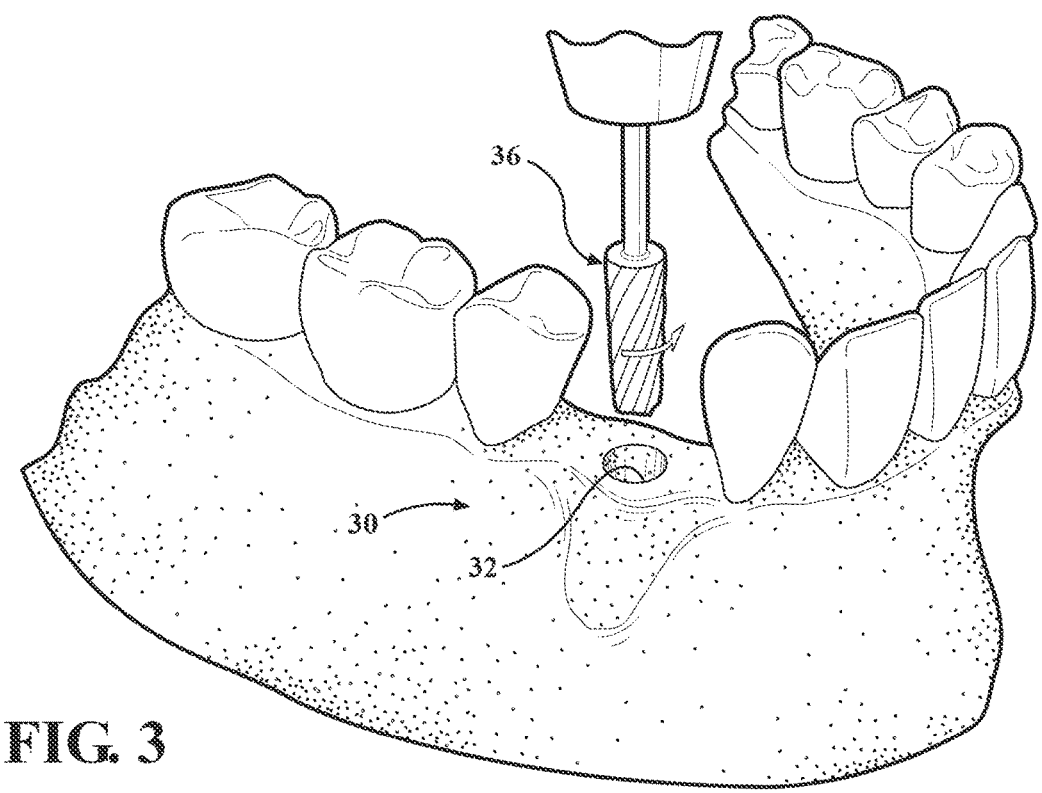
FIG. 3 is a view as in FIG. 1 showing a progressive expansion step with a rotary osteotome.
Figure 4:
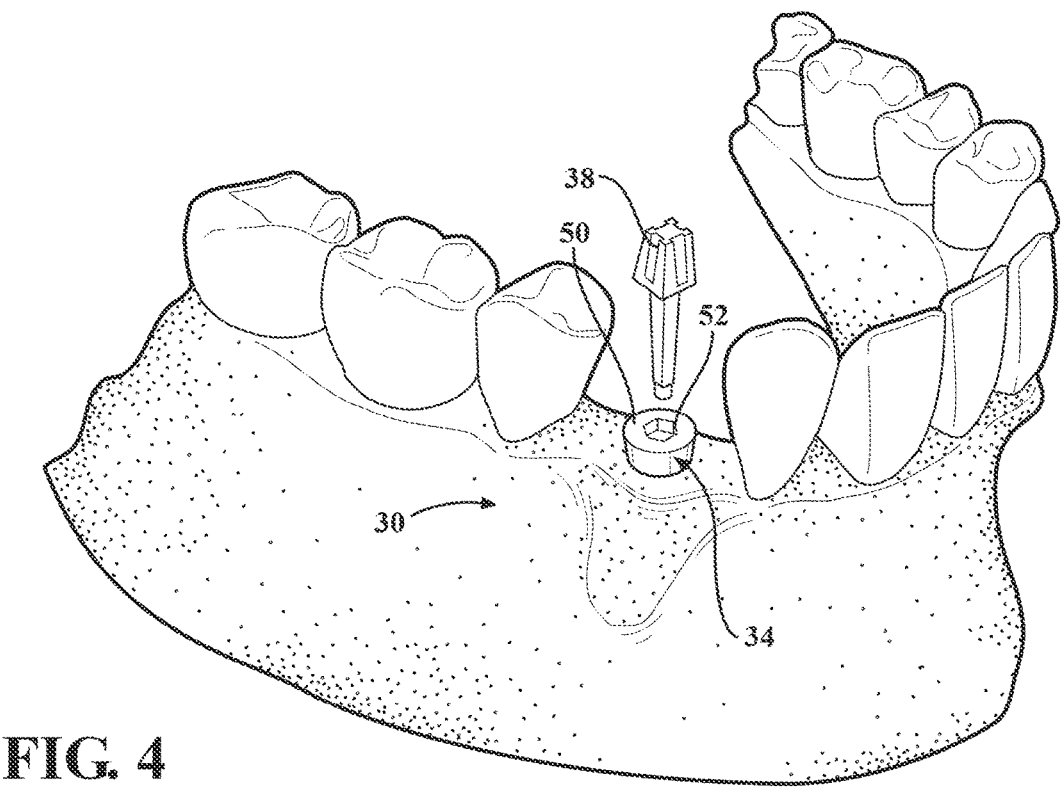
FIG. 4 is a view as in FIG. 2 in which an installed implant is poised to receive an abutment or base for subsequent prosthetic (not shown)

Referring to the figures, wherein like numerals indicate like or corresponding parts throughout the several views, FIGS. 1-4 show the example of a dental implant, in which preparation of an osteotomy is required to receive a bone implant (FIG. 4). It will be understood that this invention is not limited to dental applications, but may be applied across a wide spectrum of orthopedic applications. Furthermore, the invention is not even limited to bone or orthopedic applications, but may be used to prepare holes in metal foam and other cellular materials for industrial and commercial applications, to name but a few. Nevertheless, dental applications represent a convenient example, and so a significant portion of the following description will make use of the dental context for chiefly illustrative purposes only.

Figure 1:
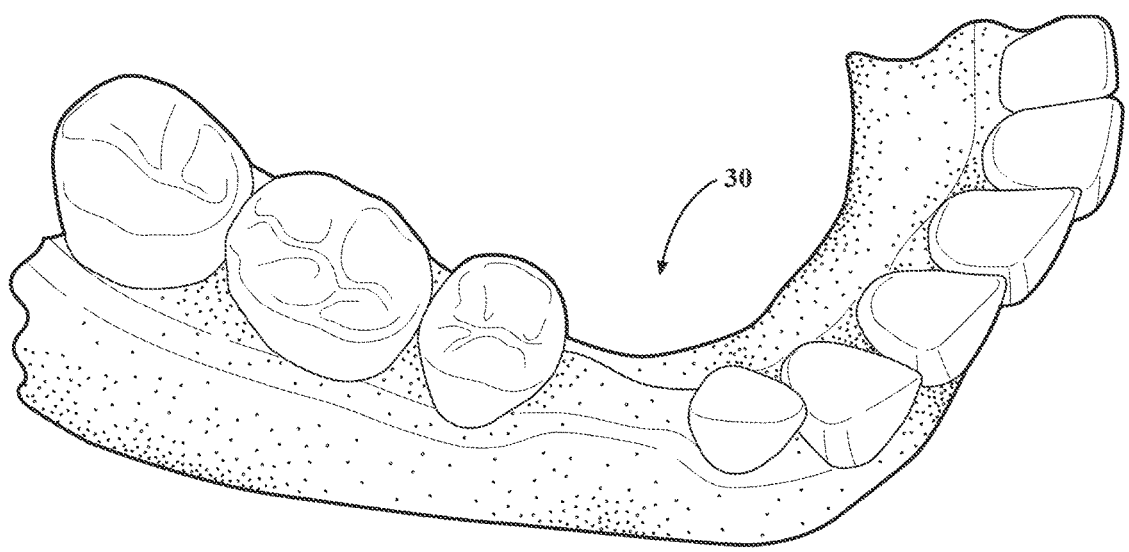
FIG. 1 depicts an exemplary application of the present invention at an edentulous (without teeth) jaw site that needs expansion to receive an implant.
Figure 2:
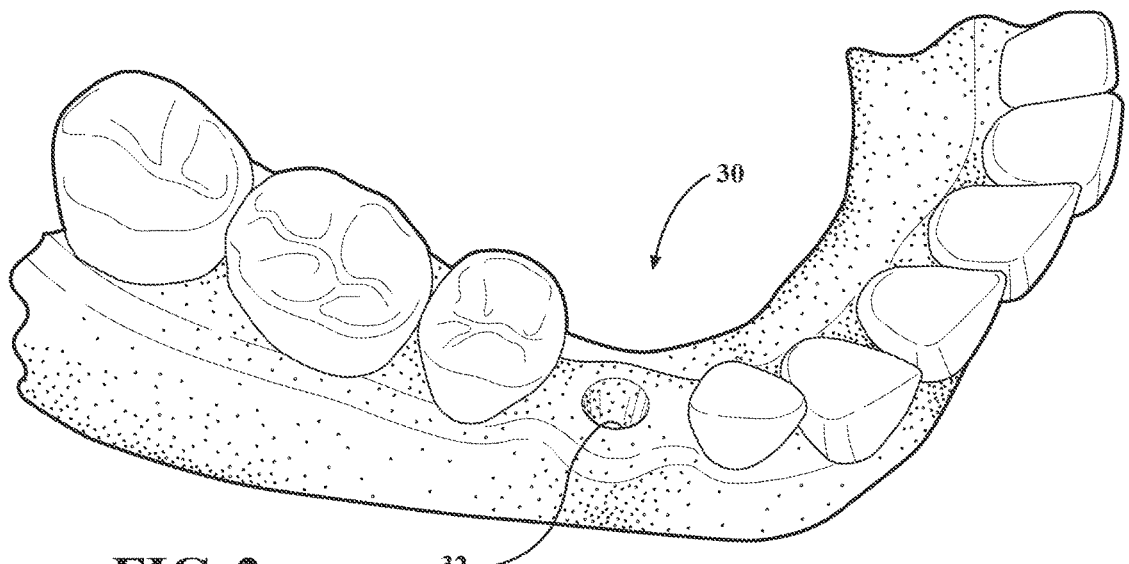
FIG. 2 is a view as in FIG. 1, but showing the resulting fully prepared osteotomy as achieved through a progressive series of expansion steps.

In FIG. 1, an edentulous (without teeth) jaw site 30 is shown that needs expanded and prepared as an osteotomy 32 (FIG. 2) in order to receive an implant, generally shown at 34 in FIG. 4. The series of steps include first boring a pilot hole or dimple into the recipient bone and then expanding the osteotomy to final size and depth using any suitable drilling or osteotome technique. One such technique comprises the use of progressively wider rotary osteotomes, generally indicated at 36, as shown in FIG. 3. The procedure of forming an osteotomy using progressively wider rotary osteotomes is described, generally, in US 2013/0004918 published Jan. 3, 2013 to Huwais, the entire disclosure of which is hereby incorporated by reference. Also incorporated herein by reference, and relied upon, is the entire disclosure of Applicant's international patent application number PCT/US13/55539 filed Aug. 19, 2013, published May 22, 2014 as WO2014/077920. Once the osteotomy has been prepared, again by any suitable technique, the implant 34 is screwed into place as illustrated in FIG. 4. An abutment 38 is threaded into an internal connect, and is thereby secured in position to receive a subsequent restoration or crown (not shown). The implant 34 is perhaps ideally suited for placement in bone, yet non-bone applications are contemplated. Although the illustrated embodiments depict the implant 34 in the form of an anchor or receptor for a subsequently installed abutment feature 38, it must be appreciated that the implant 34 may be re-configured as a bone screw or other bone fixation element as may be used for example in other orthopedic applications.

Turning now to FIGS. 5-9, the implant 34 is shown in one embodiment comprising a truncated body formed with a conically tapered outer profile. The body has an apical end 40 and a coronal end 42. The terms "apical" and "coronal" are selected primarily for their dental association. "Apical" means a direction toward the root tip(s) of a tooth; and "coronal" means a direction toward the crown of a tooth. Applicant's use of these terms and perhaps others in this document, however, must not be construed narrowly as to limit the application of the implant 34 to the dental fields of use, or even to the medical fields of use. The apical end 40 forms the leading end of the implant 34 and in use is inserted first into the prepared osteotomy 32. A central region 44 of the body extends between the apical end 40 and the coronal end 42. In practice, the longitudinal lengths of the apical end 40, coronal end 42 and central region 44 can vary relative to the entire longitudinal length of the body. For example, in the illustrated embodiment of FIG. 5, the apical end 40 is shown extending approximately ⅕ the entire longitudinal length of the body. Likewise, the coronal end 42 also extends approximately ⅕ the entire longitudinal length of the body. And the central region 44 in this example extends about ⅗ the entire longitudinal length of the body.

These dimensional relationships can be altered to suit the application and/or as to achieve specific performance attributes. For one alternative example, the apical end 40 could be changed to approximately ¼ the length of the body; the coronal end 42 shortened to ⅛ the overall length, and the central region 44 made approximately ⅝ the overall body length. In another alternative example, the apical end 40 is approximately ⅓ the length of the body; the central region 44 occupies the remaining ⅔ overall body length, and the length of the coronal end 42 made effectively negligible. Of course, many still further alternatives will become apparent to the skilled person in these arts. Notwithstanding the variable relative lengths, the outer (i.e., radial) dimensions of the sections 40-44 form a generally conical taper that enlarges toward the coronal end 42. Tapers in the range of 1°-5° are considered generally suitable for dental applications, with 2° 36' considered more or less preferred. For non-dental orthopedic applications, a somewhat larger taper range may be desired. For non-medical applications, still larger taper ranges may be considered. A conical, root-shaped geometry is believed to support superior primary stability and loading protocols. Although not shown, the extreme apex of the apical end 40 may be domed to help prevent over-insertion and/or to otherwise contribute to safer implant placement.

The apical end 40 is formed with an apical thread profile 46. The apical thread profile 46 has a right-hand twist for advancing the implant 34 progressively deeper into the osteotomy 32 as the body is forcibly turned in a clockwise direction. That is, the apical thread profile 46 forms a lead screw feature that simultaneously cuts and forges downward path in the walls of the osteotomy 32. The apical thread profile 46 has an apical pitch and an apical lead as these terms are generally understood in the context of screw threads. That is, lead is the distance along the longitudinal axis of the implant 34 that is covered by one complete rotation (360°) of the implant 34. Pitch is the distance from the crest of one thread to the next. If the apical thread profile 46 is designed as a single-start thread form, the apical lead and the apical pitch will be the same length. However, in the depicted embodiment, the apical thread profile 46 is formed as a two-start (or double-start) thread pattern, meaning that there are two non-intersecting ridges of thread profile 46 wrapped around the implant body. Each time that the implant 34 rotates one turn (360°), it advances axially by the width of two ridges, i.e., by the apical lead distance. In this case, the apical thread profile has an apical lead which is equal to twice its apical pitch, and which increases the speed at which the implant 34 is advanced into the osteotomy 32.

Figure 8:
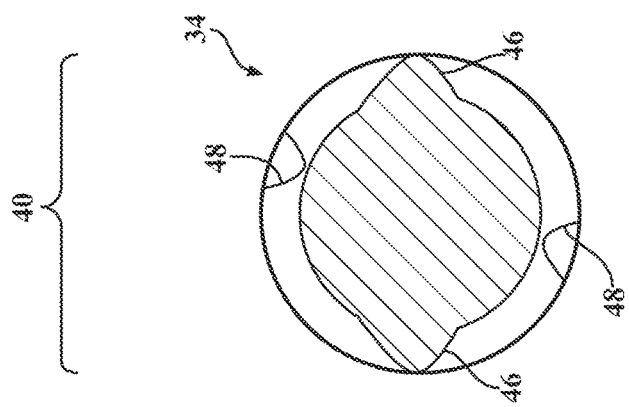
FIG. 8 is cross-section through the apical end of the implant body taken generally along lines 8-8 in FIG. 5.
Figure 7:
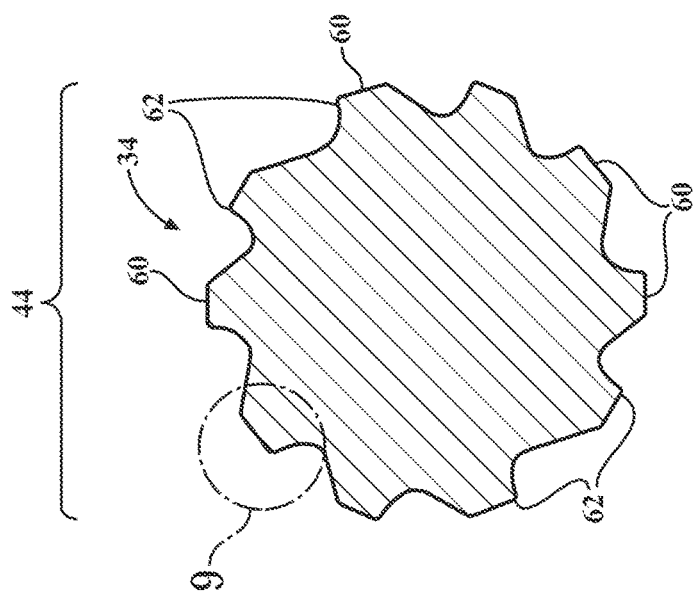
FIG. 7 is cross-section through the central region of the implant body taken generally along lines 7-7 in FIG. 5.

FIG. 8 is a cross-section (taken from FIG. 5) through the apical end 40. Here, the two-start thread pattern is clearly shown, along with the V-thread shape of the apical thread pattern which is one of several suitable alternative shapes. The apical end 40 is preferably designed so as to make the implant 34 self-tapping. Self-tapping indicates the ability for the implant 34 to advance when turned, while creating its own thread. This self-tapping ability may be facilitated by at least one self-tapping cutting edge 48. The self-tapping cutting edges 48 may be created by grinding a gap in the continuity of the threads in the apical thread profile 46. These self-tapping cutting edges 48 help cut complementary threads in the surrounding walls of the osteotomy 32 as the implant 34 is screwed in the clockwise direction. The cutting edges 48 may be considered to slice into the bone material, leaving a clean path for the screw threads to follow. In the illustrated embodiment, the apical end 40 is formed with a pair of diametrically opposed self-tapping cutting edges 48, each formed by a cut disposed in a generally helical pattern extending longitudinally toward the central region 44. These features collect and amass bone chips in the course of insertion, further supporting efficient osseointegration and long-term implant 34 stability.

Turning now to the coronal end 42, reference is made to FIGS. 5, 6, 11 and 13. The coronal end 42 comprises a platform 50 disposed centrally as a distal-most feature. In use, the platform 50 remains exposed once the implant 34 is fully seated in the osteotomy 32, as perhaps best shown in FIGS. 4 and 11. An internal connect 52 extends through the platform 50 down into the body of the implant 34. The internal connect 52 is a standard, cavity-like feature found in many prior art implant designs, and is composed of a counter bore section directly adjacent the platform 50 which extends down to an internally threaded section that is adapted to receive the threaded post of the abutment member 38 (FIG. 4). The depth of the internal connect 52 may vary, but in some dental applications typically extends to about the mid-length point of the implant 34.

Figure 5:
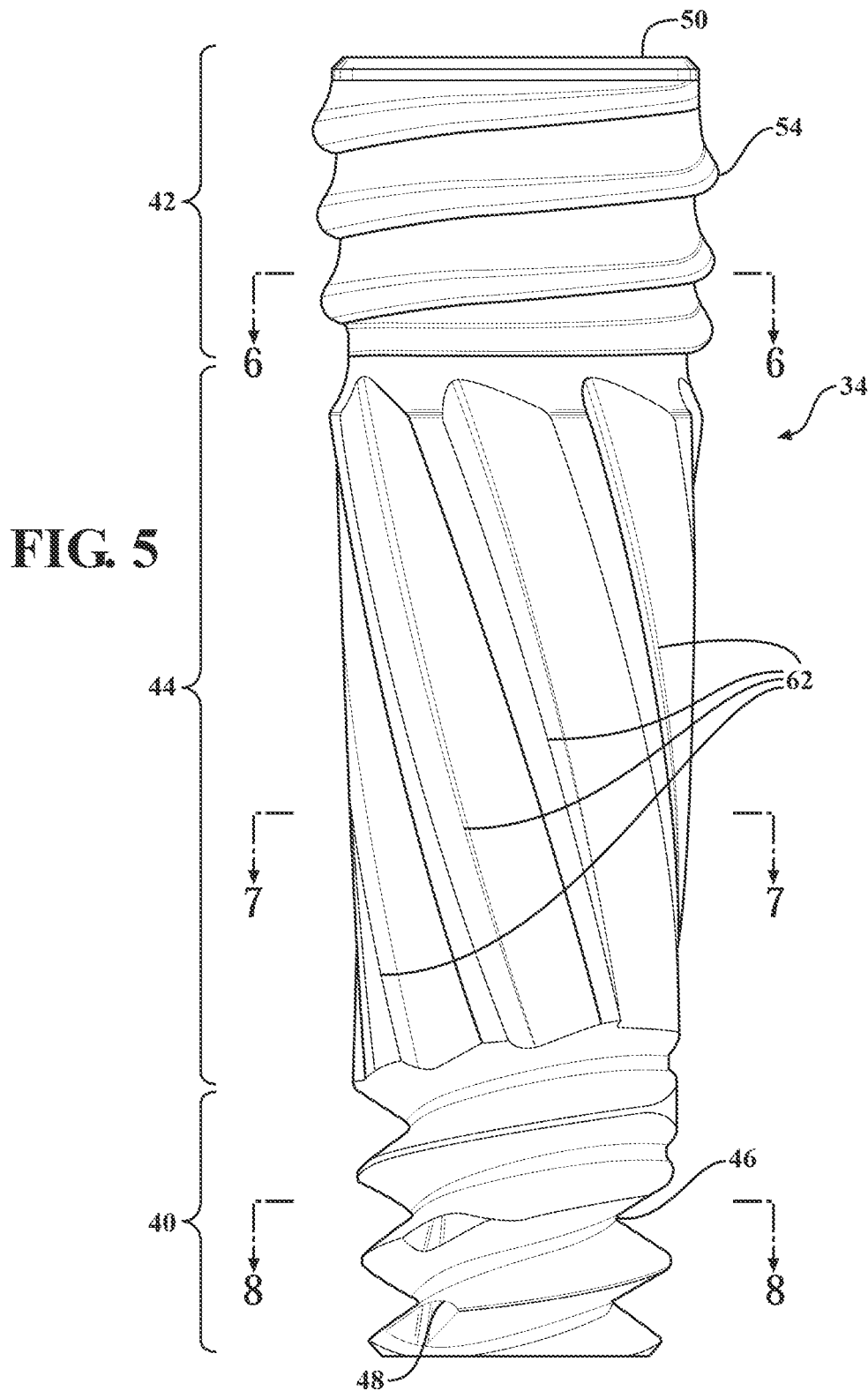
FIG. 5 is a front elevation of an implant according to one embodiment of the present invention.
Figure 6:
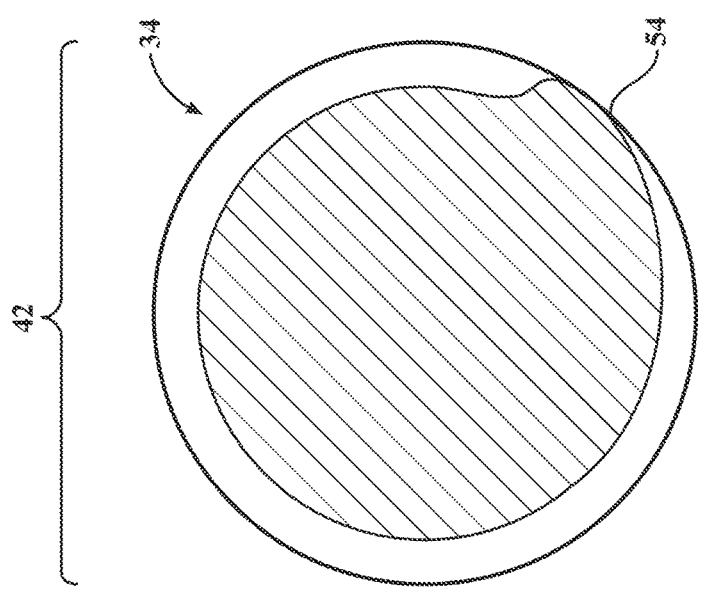
FIG. 6 is cross-section through the coronal end of the implant body taken generally along lines 6-6 in FIG. 5.

The external features of the coronal end 42 may be formed in any number of different shapes. In FIGS. 5 and 6, the coronal end 42 is shown including an optional corking element 54. The corking element 54 is designed to improve bone-to-implant contact at the crestal zone, and to help reduce, if not eliminate, instances of volcanoing or mushrooming in the bone material surrounding the osteotomy 32. The corking element 54 thus enables the installed coronal end 42 to sit neatly at or near the surface of the bone, thus yielding a better installation. The corking element 54 is mentioned as optional in that one may envision an implant 34 in which no such corking feature is incorporated into the design but which enjoys other attributes and advantages of this invention. The corking element 54 can be formed in a variety of ways to achieve similar—although perhaps somewhat varied—results. In the illustrated example of FIGS. 5, 6, 11 and 13, the corking element 54 includes a coronal thread profile having a right-hand twist. Here, the coronal thread profile is a one-start thread pattern having a pitch that is generally equal to the apical pitch. However, because in this example the coronal thread profile is a one-start formation and the apical thread profile is a two-start, the coronal lead will be only ½ the length of the apical lead. Or said another way, the coronal lead is equal to the coronal pitch.

The coronal thread profile may be configured with a buttress shape. In machinery, the buttress thread form is designed to handle extremely high axial thrust in one direction. The load-bearing thread face is perpendicular to the longitudinal axis or at a slight slant (usually no greater than 7°). The other face is slanted at 45°. As shown in FIG. 13, when the implant 34 is screwed into the osteotomy 32 to a sufficient depth, the coronal thread profile engages the inner wall of the osteotomy and begins displacing bone material in a downward (apical) wiping direction. It should be noted that because the coronal lead in this example is only ½ the apical lead, the coronal thread profile will be pulled by apical threads into the osteotomy at twice the rate at which they would otherwise tend to advance with clockwise rotation. This action causes the helical crest of the coronal thread profile to pull or scrape the bone material, including any bone material that may have already begun to mushroom up around the edges of the osteotomy 32, down into the osteotomy 32 resulting in a smoother, less disrupted surface around the osteotomy 32. As will be described below in connection with alternative embodiments, the coronal thread pattern may take many different shapes and forms.

Turning now to the central region 44, reference is made to FIGS. 5, 7 and 9-12. The central region 44 is characterized by one or more, and preferably a plurality of, trough-like flutes disposed about the body. As perhaps best illustrated by the cross-section of FIG. 7, ten flutes are shown in this example. The flutes may be equally circumferentially arranged about the body to help maintain stability during insertion. Although the flutes could be straight axial, in the preferred embodiment the flutes having a long-lead helical twist in a left-hand direction. That is to say, the flutes preferably do not have a right-hand helical twist about said body.

Figure 9:
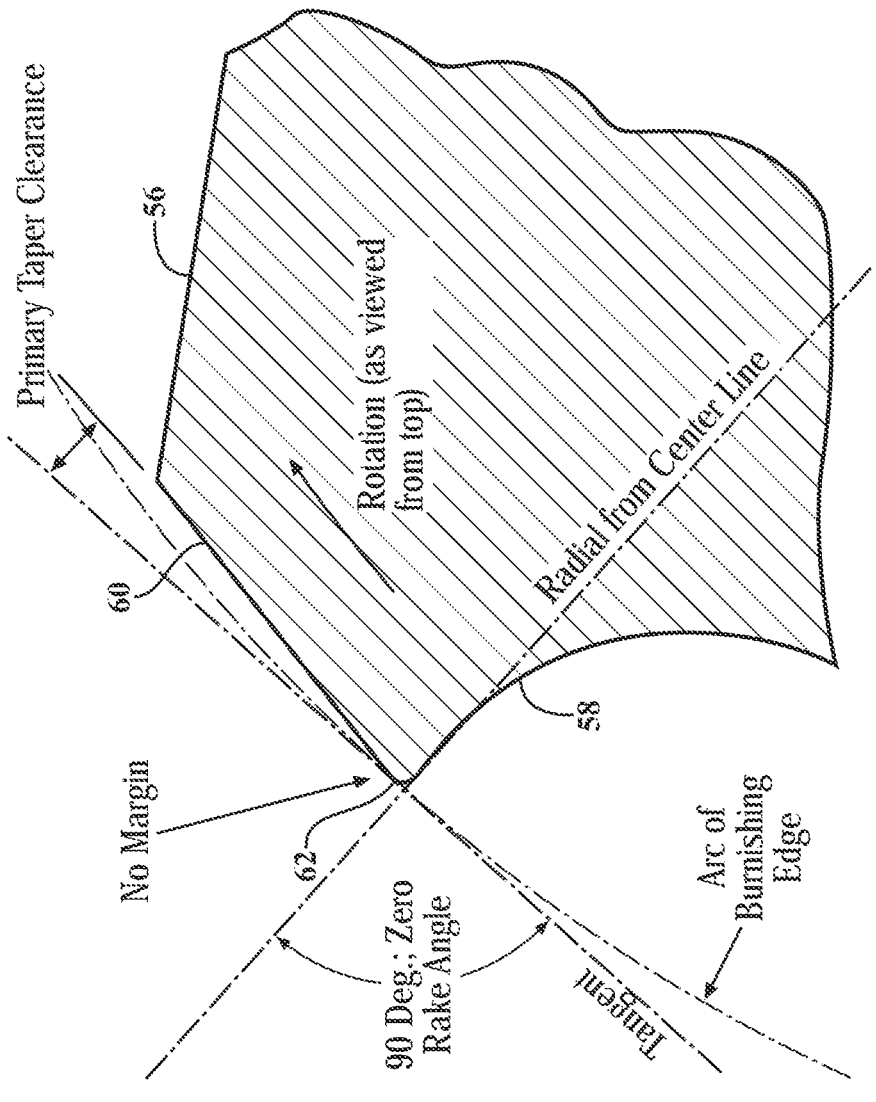
FIG. 9 is an enlarged view of a burnishing edge and associated land as circumscribed at 9 in FIG. 7.

Each flute is defined between a leading face 56 and an opposite trailing face 58. A land 60 is formed between every two adjacent flutes. As perhaps best shown in the enlarged FIG. 9, each land 60 joins or spans the trailing face 58 of one the flute and a leading face 56 of an adjacent the flute to form a ridge-like feature. At the intersection of each land 60 and the respective leading face is a burnishing edge 62. The burnishing edge 62 may be substantially margin-less, meaning that the entire portion of each land 60 falls away behind the burnishing edge 62 to provide complete clearance during rotation. In prior art drills for boring holes, for example, margins are commonly incorporated behind the cutting edges to stabilize the drill in the hole and maintain the desired drill diameter. In the preferred embodiment of this invention, such margins are not used. Instead, the land 60 tilts into the rotational direction and serves as a ramp or wedge leading the burnishing edge so that bone material is not cut from the inner wall of the osteotomy 32. The burnishing edge 62, therefore, is positioned in a non-cutting direction, meaning that its associated land 60 engages the wall of the osteotomy 32 before the burnishing edge 62. The primary taper clearance angle, i.e., the angle between a tangent of the burnishing edge 62 and each land 60 as shown in FIG. 9, may fall anywhere between about 1° and 30° depending upon the application.

Returning to FIG. 5, the burnishing edges 62 are shown extending generally the full distance between the apical thread profile 46 and the coronal thread profile, i.e., corking element 54. Like the intervening flutes, the burnishing edges 62 also preferably have a left-hand helical twist, although straight axial configurations are also possible. Long leads, on the order of 1-to-3 times the overall length of the implant body, are contemplated for the lay of the burnishing edges 62. The radial measure of each burnishing edge 62, i.e., the distance from a central axis of the implant body to the arc of the burnishing edge 62, is a function of the implant 34 taper. In this illustrated example, a substantially aligned conical taper meets the outer crests of the apical thread profile 46 and also the burnishing edges 62 and also the outer crests of the coronal thread profile. In another example, the radial measure of each burnishing edge 62 may be slightly inset from the conical taper passing through the outer crests of the apical thread profile 46 and coronal thread profile. In a still further example, the radial measure of each burnishing edge 62 may stand slightly proud of the conical taper passing through the outer crests of the apical thread profile 46 and coronal thread profile.

In use, an osteotomy 32 is prepared to receive the implant 34 when its opening at the surface of the bone has a diameter that is approximately as large as the root diameter of the extreme apex of the apical end 40. When the implant 34 is initially screwed into an osteotomy 32, its apical thread profile 46 immediately bites into the inner surface of the bone and cuts a downwardly spiraling path to quickly draw the remaining body of the implant 34 toward full seated depth. As soon as the burnishing edges 62 enter the osteotomy 32, they begin to apply a circumferentially sweeping compressive strain to the interior surface of the osteotomy 32 with a burnishing action. The further into the osteotomy 32 the implant 34 descends, the greater the degree to which the burnishing edges 62 wipe and rub against the bone to force and expansion of its inner diameter. However, because bone has elastic properties, there will be some "spring back" after the burnishing edge 62 passes by. This is illustrated in somewhat exaggerated fashion in FIG. 10. The plurality of burnishing edges 62 wiping one after another in a progressively widening manner, i.e., as the implant 34 is pulled deeper into the osteotomy 32, helps to create a compression wave ahead of the point of contact, loosely akin to spreading butter on toast. Downward pressure applied by the advancing apical thread profile 46 keeps the burnishing edges 62 in contact with the bone surface of the osteotomy 32 to maintain pressure on the compression wave. This is aided by the taper interface of the osteotomy 32 and implant 34 to create lateral pressure (i.e., in the intended radial direction of expansion).

Figure 10:
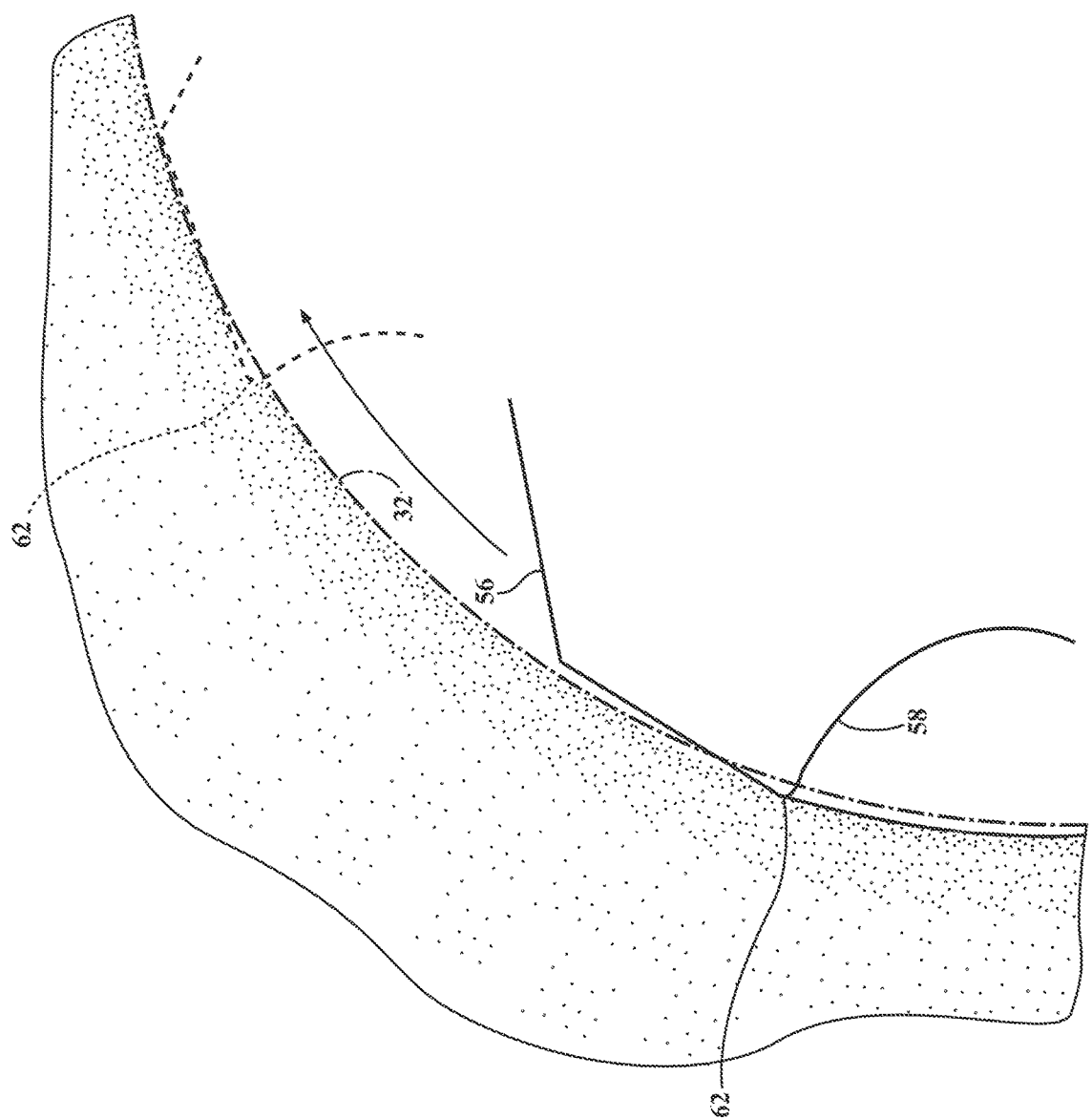
FIG. 10 is an enlarged and somewhat exaggerated view of a burnishing edge as it wipes across the inner surface of a hole displacing a semi-elastic surrounding material.
Figure 11:
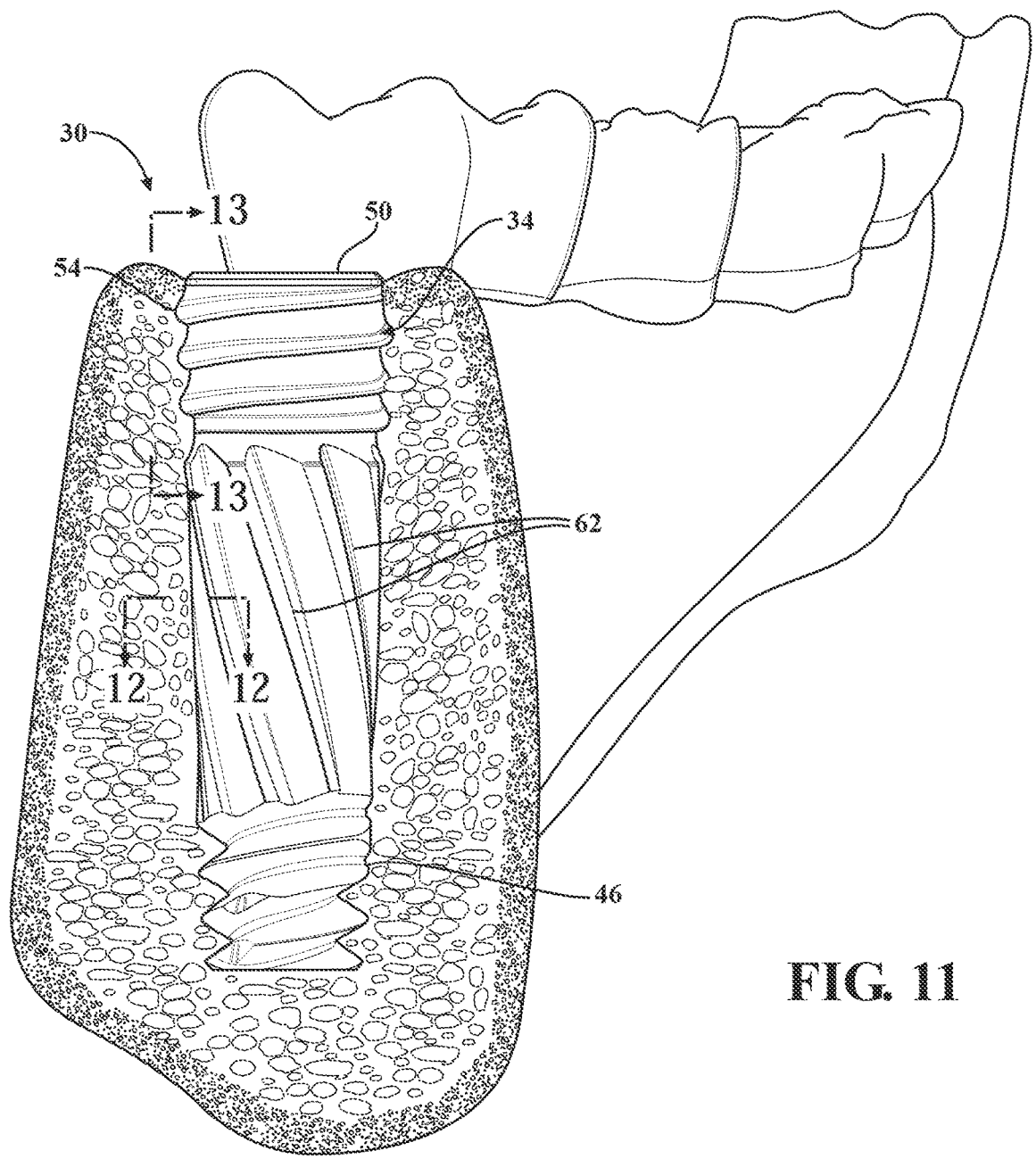
FIG. 11 is cross-section though an osteotomy in a human mandible with an implant according to one embodiment of this invention fully seated.

As the burnishing edges 62 drag across the bone, the forces on each burnishing edge 62 can be decomposed into two component forces: one normal to the bone's surface, pressing it outwardly, and the other tangential, dragging it along the inner surface of the osteotomy 32. It may be noted as well that due to the left-hand helical twist, the burnishing edges 62 will also generate a slight opposing axial reaction force when concurrently forcibly advanced into the osteotomy 32. This opposing axial reaction force works against the axial advancing direction of the implant 34 insertion by applying force in a direction that urges—but is unable due to the overwhelming grip of the apical thread profile 46—to push the implant 34 out of the osteotomy 32. As the tangential component is increased through clockwise rotation, the burnishing edges 62 slide along the bone. At the same time, the normal (i.e., radial) forces along the burnishing edges 62 will deform the softer bone material. The stresses in the bone's surface will exceed its yield strength, allowing the burnishing edges 62 to plow through the surface and create a trough behind it. The plowing action of the burnishing edges 62, as depicted in FIG. 10, thus progressively enlarges the osteotomy 32.

Stresses applied through the burnishing edges 62 continue to accumulate in the bone as the implant 34 progresses toward full seating depth in the osteotomy 32. As soon as the implant 34 reaches full depth and stops rotating, the built-up stresses in the bone begin to fill into the flutes and around the burnishing edges 62 as graphically depicted in FIG. 12. This almost immediate elastic response of the bone to the preloading of stress (from the action of the burnishing edges 62), provides a favorable high initial implant stability. Furthermore, the adapted bone into the flutes effectively self-locks the implant 34 in position so that it cannot be removed by unscrewing. Another benefit of this implant 34 with burnishing edges 62 is observed by its ability to condense and densify the surrounding bone walls of the osteotomy, thereby still further enhancing initial implant stability. A still further advantage of this implant 34 with burnishing edges 62 is its ability to strengthen the bone fabric. When bone (or wood or foam, etc.) is subjected to stress in the region between its yield point and its ultimate tensile strength, the material experiences strain hardening. Strain hardening, also known as work hardening or cold working, is the strengthening of a ductile material by plastic deformation. This strengthening occurs because of dislocation movements and dislocation generation within the crystal structure of the material. And yet another benefit of this implant 34 with burnishing edges 62 is its ability to activate natural bone re-generation through mechano-biology bone healing, where generated energy activates faster bone healing.

Figure 14:
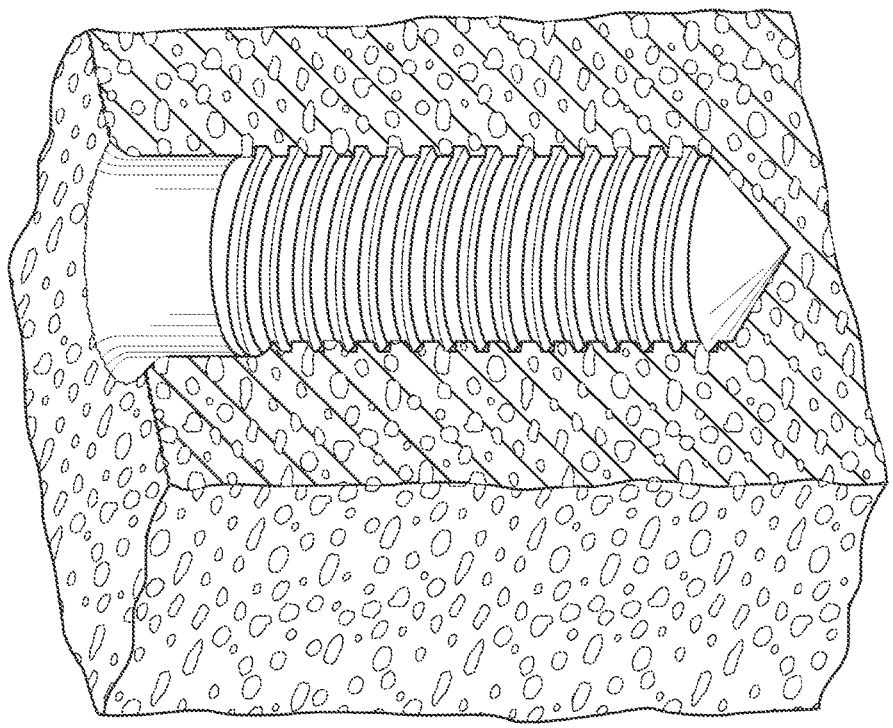
FIG. 14 represents a cross-section through an osteotomy after a typical prior art implant has been fully inserted therein, thereby leaving its impression in the bone.

FIG. 14 is a cross-section through an osteotomy after an exemplary prior art threaded-body implant has been fully inserted therein. Impressions in the bone form a more-or-less exact negative space representation around the implant. Very little space around the implant is available for bone ingrowth, such that the same cross-section taken 1-day will look essentially the same. And similarly a cross-section taken 2-4 weeks after insertion will look essentially the same as well.

Figure 15A:
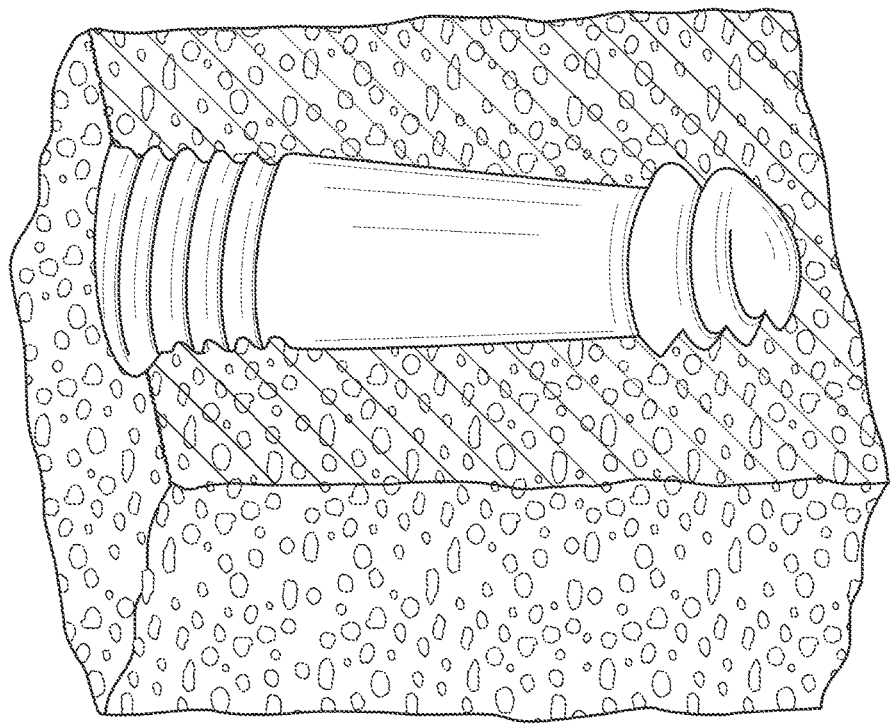
FIG. 15A represents a cross-section through an osteotomy after an implant according to one embodiment of this invention has been fully inserted therein, thereby leaving its distinctive impression in the bone.
Figure 15C:
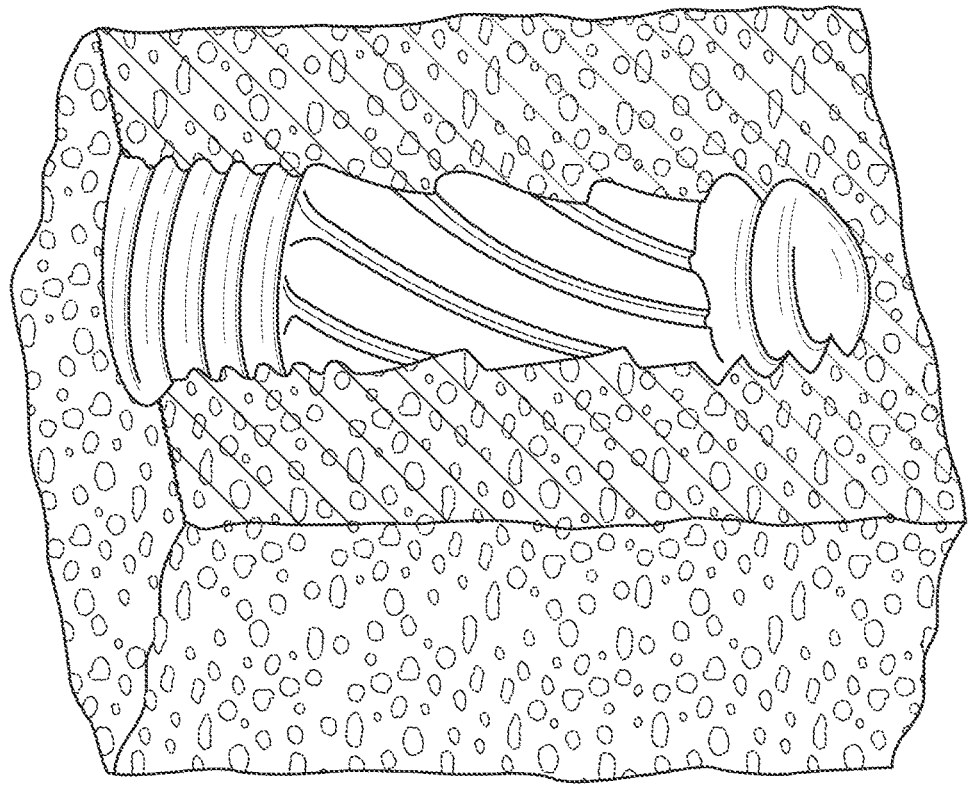
FIG. 15C is a cross-section as in FIG. 15A showing the impression left by the same implant approximately 2-4 weeks after insertion and showing essentially complete bone in-growth into crevices.
Figure 15B:
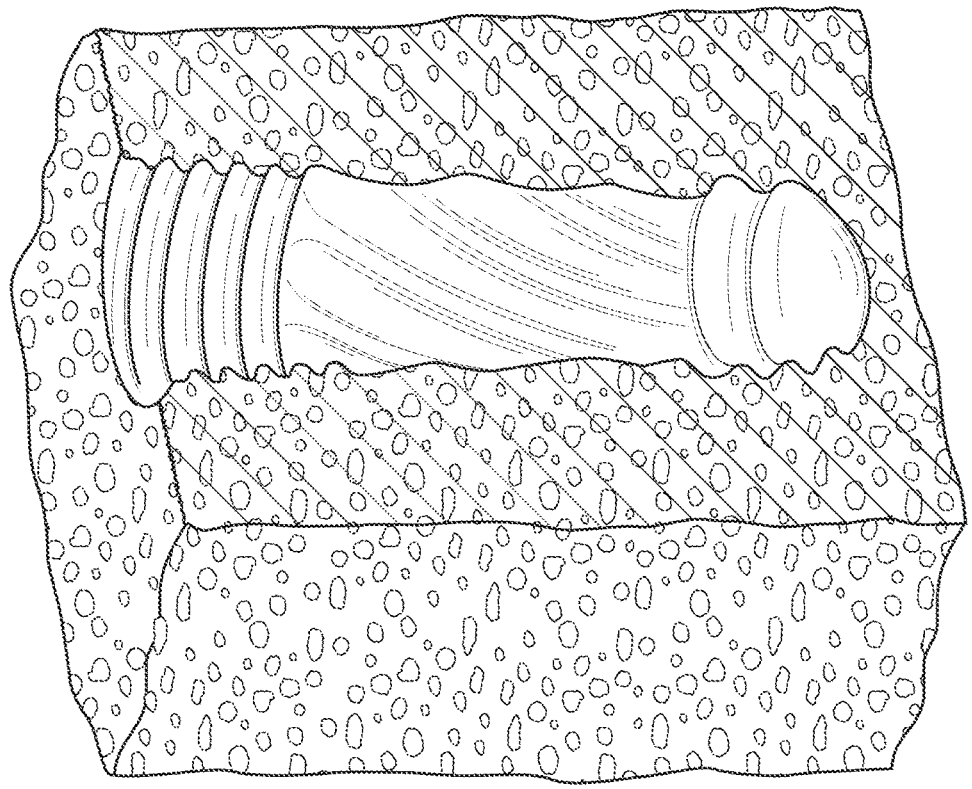
FIG. 15B is a cross-section as in FIG. 15A showing the impression left by the same implant approximately 1-day after insertion to emphasize the beginnings of bone adaptation and in-growth into crevices.

In contrast, FIG. 15A represents a cross-section through an osteotomy 32 immediately after the implant 34 of this invention has been fully seated therein. Its distinctive impression in the bone is unmistakable, particularly in the relatively smooth-walled surface formed by the sweeping rotary action of the burnishing edges 62. FIG. 15B is a cross-section as in FIG. 15A showing the impression left by the same implant 34 approximately 1-day after placement. In this view, the beginnings of bone swelling and in-growth into crevices between the lands 60 and crestal thread forms of the corking element 54 are evident. Bone swelling around the central region 44 of the implant 34 effectively self-locks the implant 34 within the osteotomy 32 even at this very early stage of placement thus making even a little loosening of the implant 34 virtually impossible. At least some load-carrying capacity of the implant 34 should be possible. FIG. 15C shows the impression left by the same implant 34 approximately 2-4 weeks after insertion. In normal, healthy bone, nearly complete bone in-growth into the crevices of the implant 34 will occur. The implant 34 is fully mechanically locked in the bone at this stage; healing is effectively complete.

Figure 16:
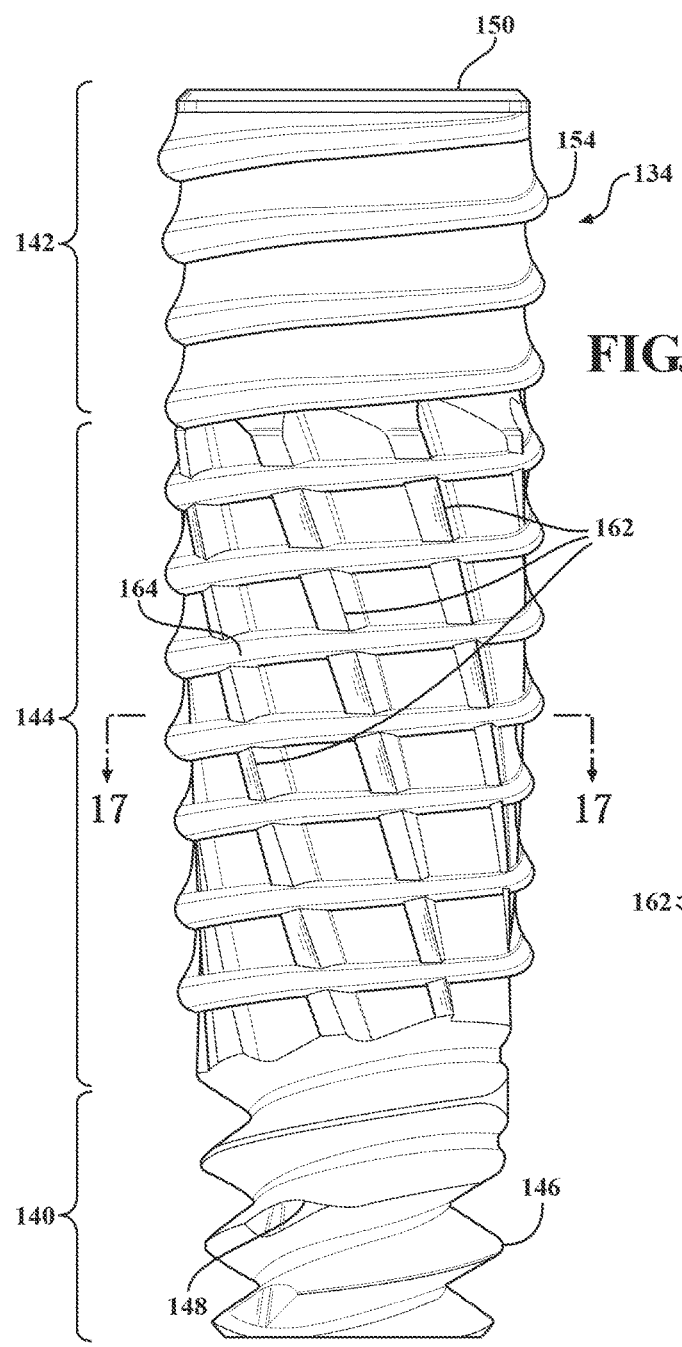
FIG. 16 is a front elevation of an implant according to a first alternative embodiment of the present invention.
Figure 17:
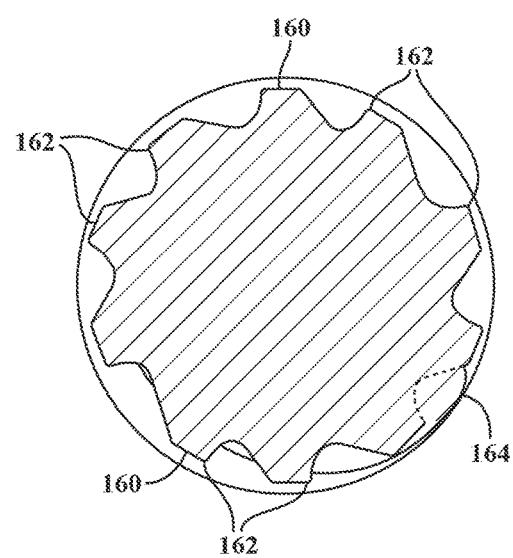
FIG. 17 is cross-section taken generally along lines 17-17 of FIG. 16.

FIGS. 16 and 17 show a first alternative embodiment of the present invention. In this example, features of the implant corresponding to those described above are identified with like reference numerals but offset by 100. According, in this embodiment, the implant 134 is shown having a generally similar truncated body formed with a conically tapered outer profile. The body has an apical end 140 and a coronal end 142 and a central region 144. An apical thread profile 146 is characterized by an aggressive, self-tapping V-shaped two-start design, whereas a corking element 154 is included in the form of a coronal thread profile having a one-start thread pattern in a buttress style. A plurality of burnishing edges 162 extend with a left-hand helical twist along the central region 144. Of unique detail in this embodiment is a central thread profile 164 that intersects the burnishing edges 162. The central thread profile 164 is shown in these views as a continuation of the buttress style coronal thread profile of the corking element 154. The combined coronal thread profile and central thread profile 164 extend, generally uninterrupted, from the coronal end 142 to the apical thread profile 146 but without overlapping the apical thread profile 146. As a continuation of the coronal thread profile, the central thread profile 164 also has a right-hand twist, and a central lead which is equal to its central pitch which is also generally equal to the coronal pitch.

The conically tapered outer profile of the implant 134 is defined by the crests, i.e., outermost helical ridges, of the apical thread profile 146 and the central thread profile 164 and the coronal thread profile. That is, in this embodiment the crests of the coronal, central and apical thread profiles are generally aligned along a conical taper that defines the overall conical taper of the implant 134. As perhaps best shown in FIG. 17, the radial measure of each burnishing edge 162 is slightly inset from the conical taper established by the outer crest of the central thread profile 164. As such, the central thread profile 164 stands slightly proud of the burnishing edges so that, in use, the above-described corking action is performed by the central thread profile 164 as well as the coronal thread profile. In this example, the lead of the apical thread profile 146 remains approximately twice that of the lead of the integrated coronal and central 164 thread profiles so the latter thread profiles are pulled into an osteotomy at twice the rate at which they would otherwise tend to advance with clock-wise rotation of the implant 134. This fast-pulling action causes the helical crest of the coronal and central 164 thread profiles to displace bone material in a downward (apical) wiping direction.

Meanwhile, the burnishing edges 162 apply a circumferentially sweeping compressive strain to the interior surface of the osteotomy with the above-described burnishing action. As the implant 134 descends into the osteotomy, the burnishing edges 162 wipe and rub against the bone with a progressively greater effect, interrupted at regular intervals by the central thread profile 164, as the central thread profile 164 concurrently displaces bone material in a downward wiping direction. When the burnishing edges 162 are formed with a left-hand helical twist as shown in FIG. 16, i.e., as opposed to a straight axial (infinite lead) shape, a slight opposing axial reaction force will be generated by the burnishing edges 162 dragging across the bone surface. The combination of reaction force components (normal, tangential and axial) cooperate to stress the bone material beyond its yield strength, allowing the burnishing edges 162 to plow through the surface and progressively enlarge the osteotomy while concurrently accumulating stresses in the bone. By somewhat imperfect analogy, one may think of a propeller placed in water and rotated rapidly enough to displace all water from around the propeller blades. But once the propeller stops rotating, the surrounding water rushes in to fill the spaces around the blades. In the present case, the burnishing edges 164 are like the propeller blades pushing the bone material outwardly. When the implant 134 reaches full depth and stops rotating, accumulated stresses in the bone begin to fill into the flutes and around the burnishing edges 62; not to the speed or degree that water would in the suggested analogy, but more like that illustrated in FIG. 12. This almost immediate elastic response of the surrounding bone self-locks the implant 34 in position so that it cannot be unscrewed thereby providing the implant 134 with high initial stability. And naturally, all of the other aforementioned benefits of the burnishing edges 162 also persist.

Figure 18:
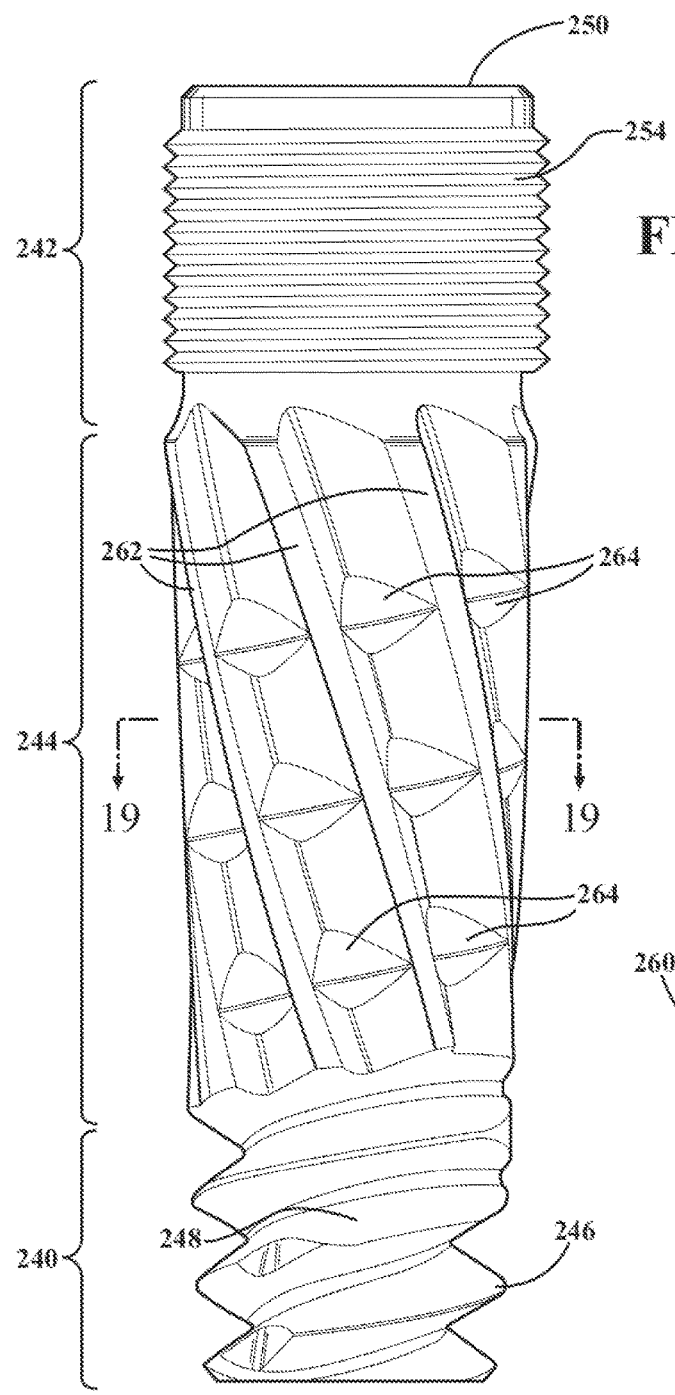
FIG. 18 is a front elevation of an implant according to a second alternative embodiment of the present invention.
Figure 19:
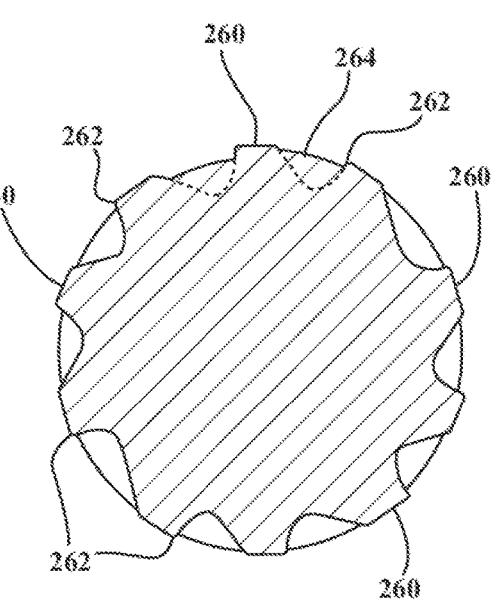
FIG. 19 is cross-section taken generally along lines 19-19 of FIG. 18.

FIGS. 18 and 19 show a second alternative embodiment of the present invention. In this example, features of the implant corresponding to those described in the preceding example are identified with like reference numerals but with a 2-prefix rather than a 1-prefix. According to this second alternative embodiment, the implant 234 is shown having a generally similar truncated body formed with a conically tapered outer profile. The body has an apical end 240 and a coronal end 242 and a central region 244. The apical thread profile 246 is again characterized by an aggressive, self-tapping V-shaped two-start design, whereas a corking element 254 is included in the form of micro-grooves having a stacked-annular (i.e., non-threaded) pattern. A plurality of burnishing edges 262 extend with a left-hand helical twist along the central region 244. A central thread profile 264 intersects the burnishing edges 262. The central thread profile 264 is shown in this example as a partial continuation of the apical thread profile 246. More specifically, the apical thread profile 246 remains a two-start formation, but only one of its two thread wraps are continued into the central region 244 as the central thread profile 264. The one shared thread profile extends from the apical end 240 into the central region 244 generally uninterrupted. As a continuation of one apical thread profile 246, the central thread profile 264 also has a right-hand twist, and a central lead which is equal to its central pitch but double that of the apical pitch formed by a two-start thread wrap. Said another way, the central lead is generally equal to the apical lead, but the central pitch is twice that of the apical pitch.

In this second alternative embodiment, the conically tapered outer profile of the implant 234 is defined by the crests of the apical thread profile 246 and the burnishing edges 262 and the micro-grooves of the corking element 254. That is, in this embodiment the crests of the apical thread profiles 246 and the burnishing edges 264 and the crests of the micro-grooves are generally aligned along a conical taper that defines the overall conical taper of the implant 234. As perhaps best shown in FIG. 19, the radial measure of each burnishing edge 262 is slightly outset from the outer crest of the central thread profile 264. As such, the burnishing edges 262 stand slightly proud of the central thread profile 264 so that, in use, the burnishing edges 262 apply a circumferentially sweeping compressive strain to the interior surface of the osteotomy with the above-described burnishing action, interrupted at intervals by the central thread profile 264. Also, the above-described corking action is performed by the micro-grooves of the coronal corking element 254. In this example, the lead of the apical thread profile 146 is equal or generally equal to the lead of the integrated central thread profile 264 so the latter thread profile follows a track cut by the apical thread profile 246 as the implant 234 is pulled into an osteotomy with clock-wise rotation. Accordingly, the central thread profile 264 helps the apical thread profile 246 to advance the implant 234 deeper into the osteotomy. As the implant 234 descends into the osteotomy, the burnishing edges 262 wipe and rub against the bone with a progressively greater effect akin the preceding examples. Also, the corking element 254 in the form of micro-grooves provides the aforementioned corking function for the implant 234 during its final approach to full seating depth.

Figure 20:
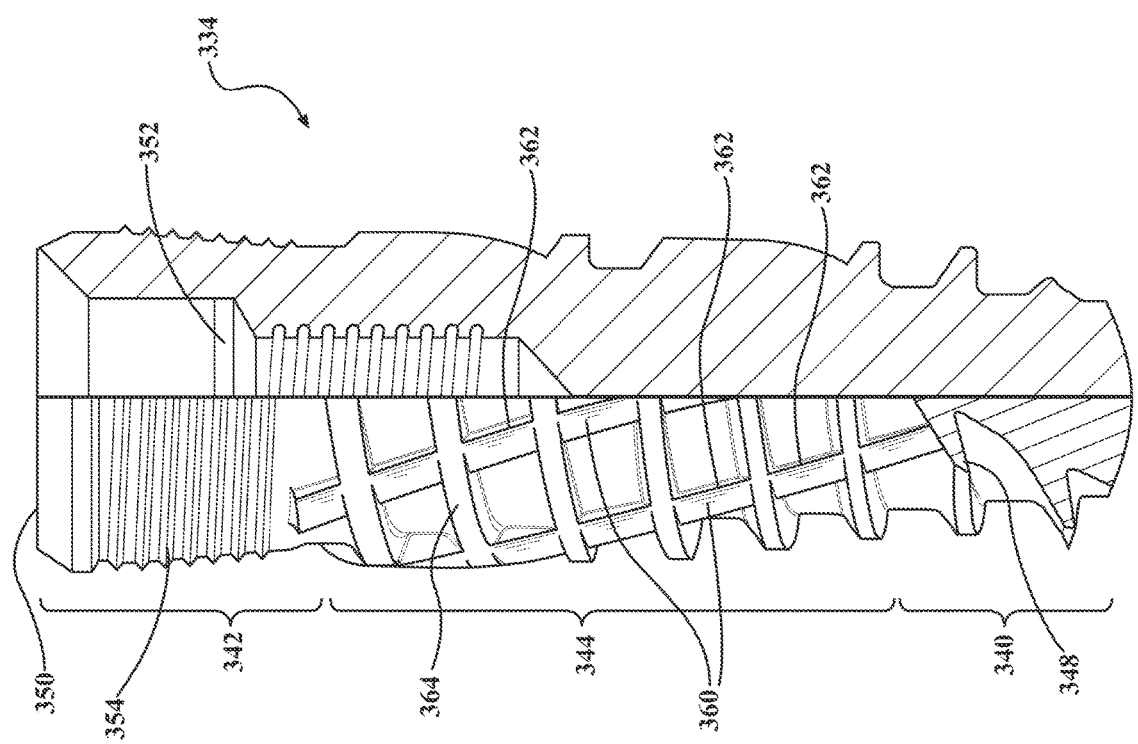
FIG. 20 is a front elevation shown in quarter-section of an implant according to a third alternative embodiment of the present invention.

FIG. 20 shows a third alternative embodiment of the present invention. In this example, features of the implant corresponding to those described in the preceding example are identified with like reference numerals but with a 3-prefix rather than a 2-prefix. Also, FIG. 20 depicts the implant 334 in quarter-section so that the internal connect 352 is clearly visible. This third alternative embodiment again shows an implant 334 having a generally similar truncated body formed with a conically tapered outer profile. The body has an apical end 340 and a coronal end 342 and a central region 344. The apical thread profile 346 in this embodiment is shown with an aggressive, self-tapping square-shaped, semi-buttress two-start design. The corking element 354 is shown here as micro-threads. A plurality of burnishing edges 362 extend with a left-hand helical twist along the central region 344. A central thread profile 364 intersects the burnishing edges 362. As in the immediately preceding example, the central thread profile 364 is a natural continuation from the apical thread profile 346. However, unlike the preceding example both of the thread wraps from the two-start apical thread profile 246 are continued, uninterrupted, through the central region 344. That is to say, the apical thread profile 346 remains a two-start formation throughout the central region 344. As a continuation of apical thread profile 346, the central thread profile 364 also has a right-hand twist, and a central lead which is equal to two-times its central pitch. The central lead is generally equal to the apical lead.

In this third alternative embodiment, the conically tapered outer profile of the implant 334 is defined by the crests of the apical/central thread profiles 346, 364 and the burnishing edges 362 and the micro-threads of the corking element 354. The radial measure of each burnishing edge 362 is generally equal to the outer crest of the central thread profile 364. As such, the burnishing edges 362 meet at the crests of the central thread profiles 364. In use, the burnishing edges 362 apply a circumferentially sweeping compressive strain to the interior surface of the osteotomy with the above-described burnishing action and are interrupted at regular times in the rotation by the central thread profile 364. Also, the above-described corking action is performed by the micro-threads of the coronal corking element 354. In this example, the integrated central thread profile 364 follows a track cut by the apical thread profile 346 as the implant 334 drives itself into an osteotomy with clock-wise rotation, and therefore contributes to pulling the implant 334 deeper into the osteotomy. As the implant 334 descends into the osteotomy, the burnishing edges 362 wipe and rub against the bone with a progressively greater effect as previously described.

Figure 22:
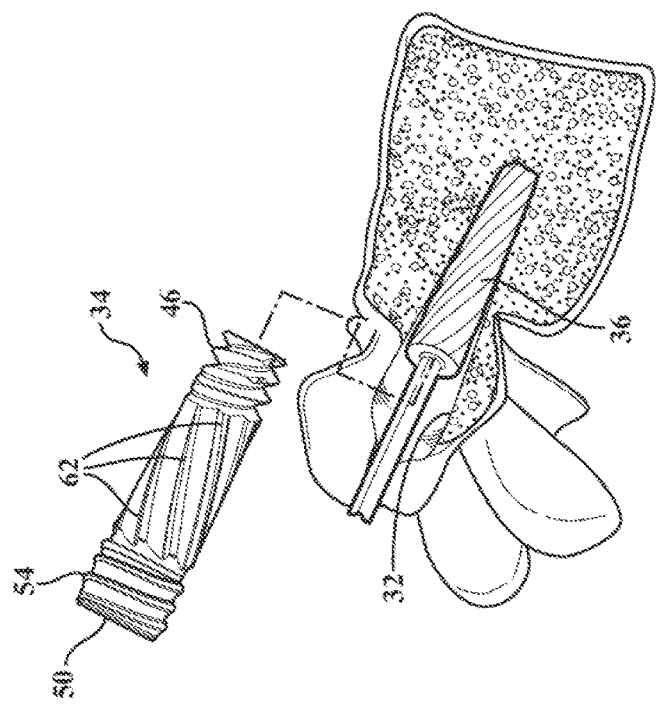
FIG. 22 is an enlarged view of a human vertebrae shown in partial cross-section with a rotary osteotome disposed to enlarge an osteotomy therein to receive an implant according to the present invention.
Figure 21:
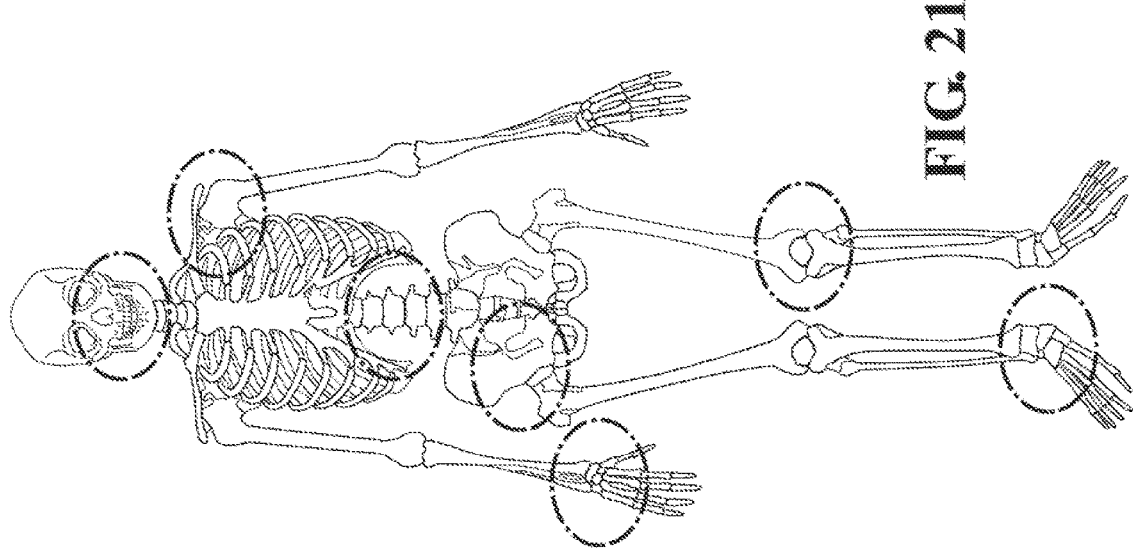
FIG. 21 is a simplified depiction of a human skeleton highlighting some examples of the many possible areas in which the novel implant of this invention might be effectively applied.

FIGS. 21-22 are intended to illustrate, for the benefit of the skilled artisan, that the principles of this invention are not limited to dental applications, but may be readily extended to any bone preparation site within the human (or animal) body with suitable adjustments in scale and/or configuration. Regions shown circled in the human skeleton of FIG. 21 represent a few of potentially many areas that are likely to benefit from application of the teachings of this present invention. Initial indications reveal that applications in the vertebrae (FIG. 22) are prime candidates for the burnishing implant and techniques of this invention due to its potential for universally applicable increases in implant primary stability and inherent similarity to prior art implant placement techniques.

Figure 23:
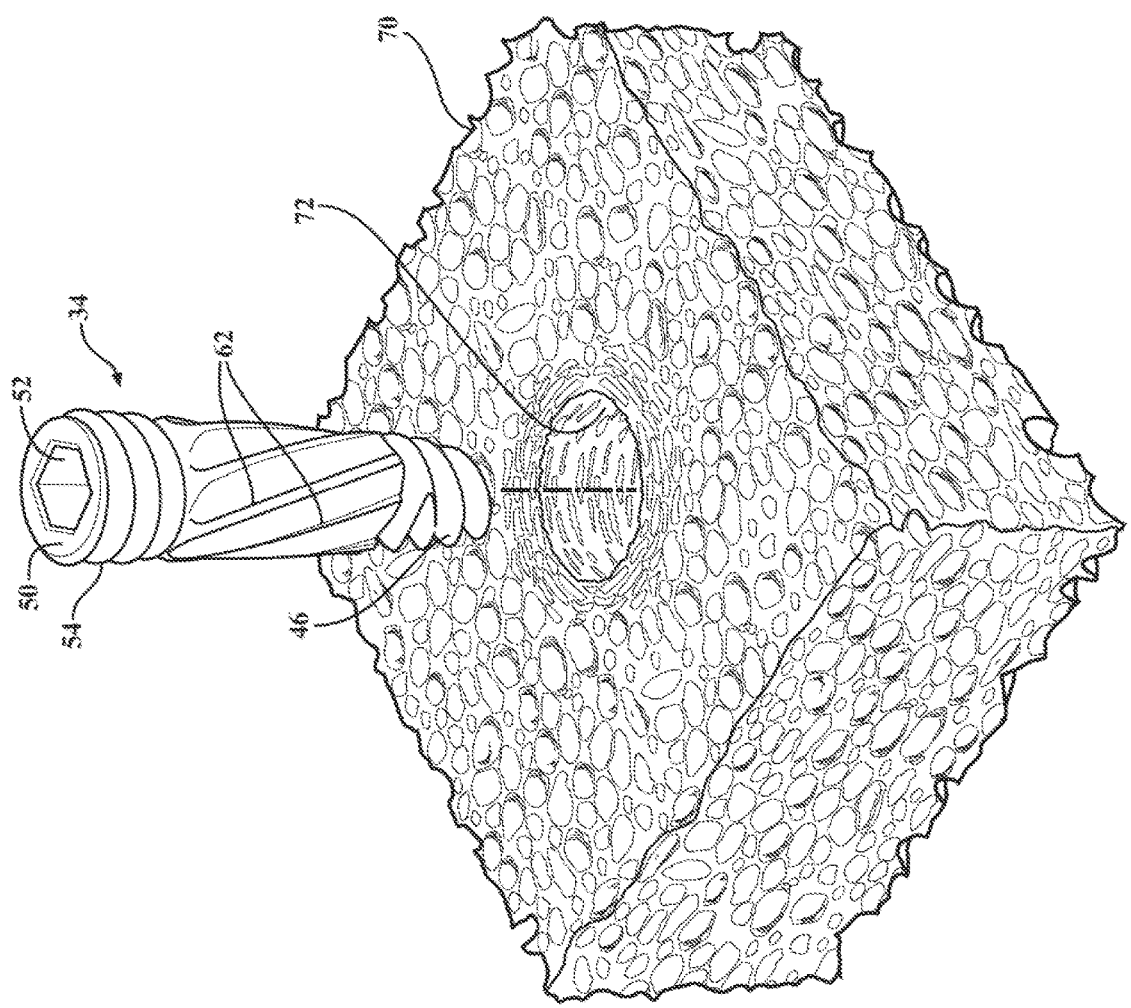
FIG. 23 is a perspective view of a foam metal product having a hole formed therein and poised to receive an anchoring implant exemplifying at least one non-bone commercial application of the present invention.

Furthermore, as shown in FIG. 23 the principles of this invention are not limited to bone as the host material. Indeed, the burnishing implant 34 of this invention may be configured to establish an anchor in almost any type of cellular material or non-cellular material that has suitable elastic response characteristics as in the bone example given above so that when the implant 34 reaches full depth and stops rotating, accumulated stresses in the surrounding material begin to fill into the flutes and around the burnishing edges 62 more-or-less like that illustrated in FIG. 12. This elastic and/or healing response of the surrounding material self-locks the implant 34 in position so that it cannot be unscrewed thereby providing the implant 34 with high initial stability. For example, the implant 34 may be used as an anchor in wood—both dried and green. When used as an anchor in a live tree, the living cells of the wood will grow into the crevices of the implant 34 in an analogous way to the bone adaptation and in-growth described above to provide a beneficial interlocking characteristic. In FIG. 12, a section of metal foam 70 may be of the type used extensively in aerospace, heat shielding and other critical applications. The foam metal 70 is shown including a hole 72 formed by burnishing according to the methods described above or by simple drilling. If the hole 72 is formed by burnishing according to the methods described, the resulting hole 72 is better prepared to receive the implant 34 because its inner walls have been densified by the compressive displacement and/or auto-grafting effects of that specialized technique. The Applicant further contemplates application of the implant 34 to civil engineering scenarios including anchors in earthen holes in soft, loose soils and muck, etc. Indeed many other applications may also present due to the unique burnishing qualities of the implant 34.

Throughout this description, reference is made to right-hand and left-hand threads. Right-hand threads advance under clockwise rotation and conversely left-hand threads advance under counter-clockwise rotation. Right-hand threads are by overwhelming proportion most common and therefore such usage has been carried throughout this description. It should be understood, however, that reversal of all thread patterns from right-handed to left-handed and (vise-versa) is possible in this implant 34 and will result in substantially identical performance characteristics with counter-clockwise rotation upon insertion. Left-handed twist for the apical thread profile 46 is thus considered a mere structural equivalent to the disclosed and claimed embodiments herein. Said another way, if one of the clockwise or counter-clockwise directions are deemed a "first" rotatory direction and the other of the clockwise and counter-clockwise directions are deemed a "second" rotary direction, then it would be accurate to say that if the apical thread profile 46, 146, 246, 346 is formed in the first rotary direction, then preferably the helical twist of the burnishing edges 62, 162, 262, 362 are preferably in the second rotary direction or straight (infinite lead) and angled in a non-cutting direction so as not to cut material from the inner wall of the osteotomy 32.

The foregoing invention has been described in accordance with the relevant legal standards, thus the description is exemplary rather than limiting in nature. Variations and modifications to the disclosed embodiment may become apparent to those skilled in the art and fall within the scope of the invention.

What is claimed is:

1. A bone implant of the type screwed into an osteotomy having an interior surface, said implant comprising:
    a body having a conically tapered profile, said body including an apical end and a coronal end, a central region of said body extending between said apical end and said coronal end,
    said apical end having an apical thread profile for advancing said body progressively deeper into the osteotomy as said body is forcibly turned in a first rotary direction,
    characterized by
    said central region including at least one radially protruding and longitudinally extending burnishing edge configured to apply a circumferentially sweeping compressive strain to the interior surface of the osteotomy with a burnishing action while said implant is being screwed into position.

2. The implant of claim 1 wherein said apical thread profile has a right-hand twist and said burnishing edge has a left-hand helical twist.

3. The implant of claim 1 wherein said burnishing edge is substantially margin-less, said burnishing edge configured to generate an opposing axial reaction force when forcibly advanced into the osteotomy.

4. The implant of claim 1 wherein said apical thread profile has a right-hand twist and said burnishing edge has a left-hand helical twist, and wherein said central region includes a plurality of flutes disposed about said body, said flutes having a left-hand helical twist corresponding to said left-hand twist of said burnishing edge, said at least one burnishing edge comprising a plurality of substantially identical burnishing edges, each said burnishing edge formed between two adjacent said flutes.

5. The implant of claim 4 further including a plurality of lands, each said land formed between two adjacent flutes, each said land extending directly from one of said burnishing edges into said first rotary direction.

6. The implant of claim 1 further including a central thread profile intersecting said burnishing edge, said central thread profile having a helical twist in the first rotary direction.

7. The implant of claim 6 wherein said central thread profile has a crest, said burnishing edge standing proud of said crest at each point of intersection therebetween.

8. The implant of claim 6 wherein said central thread profile comprises a one-start thread pattern.

9. The implant of claim 6 wherein said apical thread profile has a right-hand twist and said burnishing edge has a left-hand helical twist, and wherein said coronal end includes a corking element, said corking element includes a coronal thread profile, said coronal thread profile having a right-hand twist, said coronal thread profile having a coronal pitch, and wherein said central thread profile has a central pitch, said central pitch generally equal to said coronal pitch.

10. The implant of claim 6 wherein said apical thread profile has an apical lead, and wherein said central thread profile has a central lead, said central lead is equal to said apical lead.

11. An implant of the type screwed into an hole, said implant comprising:
    a body having a conically tapered profile, said body including an apical end and a coronal end, a central region of said body extending between said apical end and said coronal end,
    said apical end having an apical thread profile, said apical thread profile defined by a helical twist in a first rotary direction for advancing said body progressively deeper into the hole as said body is forcibly turned in the first rotary direction,
    characterized by
    said central region including a plurality of radially protruding burnishing edges each configured to apply a circumferentially sweeping compressive strain to the interior surface of the hole with a burnishing action while said implant is being screwed into position.

12. The implant of claim 11 wherein said first rotary direction is clockwise, and wherein said apical thread profile has a right-hand twist and said burnishing edges each have a left-hand helical twist.

13. The implant of claim 11 wherein each said burnishing edge is substantially margin-less, and each said burnishing edge configured to generate an opposing axial reaction force when forcibly advanced into the osteotomy.

14. The implant of claim 11 wherein said central region includes a plurality of flutes disposed about said body, each said burnishing edge formed between two adjacent said flutes, further including a plurality of lands, each said land formed between two adjacent flutes, each said land extending directly from one of said burnishing edges into said first rotary direction.

15. The implant of claim 11 further including a central thread profile intersecting said burnishing edge, said central thread profile having a helical twist in the first rotary direction.

16. The implant of claim 15 wherein said apical thread profile has a right-hand twist and said burnishing edge has a left-hand helical twist, and wherein said coronal end includes a corking element, said corking element includes a coronal thread profile, said coronal thread profile having a right-hand twist, said coronal thread profile having a coronal pitch, and wherein said central thread profile has a central pitch, said central pitch generally equal to said coronal pitch.

17. A method for screwing an implant into an osteotomy having an interior surface, said method comprising the steps of:
inserting an apical end of an implant body into an opening of an osteotomy,
screwing the body progressively deeper into the osteotomy,
characterized by
applying a circumferentially sweeping compressive strain to the interior surface of the osteotomy with at least one radially protruding burnishing edge concurrently with said screwing step.

18. The method of claim 17, wherein said step of applying a circumferentially sweeping compressive strain includes concurrently generating normal and tangential and axial reaction forces against the at least one burnishing edge, the axial reaction forces urging the implant out of the osteotomy.

19. The method of claim 17, further including the step of interrupting the circumferentially sweeping compressive strain to the interior surface of the osteotomy with a central thread profile.

20. The method of claim 19, wherein said step of interrupting the circumferentially sweeping compressive strain includes displacing bone material in a wiping direction with the central thread profile.

* * * * *